US010996216B2

(12) United States Patent
Arai

(10) Patent No.: US 10,996,216 B2
(45) Date of Patent: May 4, 2021

(54) METHOD FOR SEPARATING CELLS, AND DEVICE THEREFOR

(71) Applicant: TOPPAN PRINTING CO., LTD., Tokyo (JP)

(72) Inventor: Noriaki Arai, Tokyo (JP)

(73) Assignee: TOPPAN PRINTING CO., LTD., Tokyo (JP)

( * ) Notice: Subject to any disclaimer, the term of this patent is extended or adjusted under 35 U.S.C. 154(b) by 732 days.

(21) Appl. No.: 15/552,254

(22) PCT Filed: Feb. 26, 2016

(86) PCT No.: PCT/JP2016/001055
§ 371 (c)(1),
(2) Date: Aug. 18, 2017

(87) PCT Pub. No.: WO2016/136273
PCT Pub. Date: Sep. 1, 2016

(65) Prior Publication Data
US 2018/0038876 A1  Feb. 8, 2018

(30) Foreign Application Priority Data

Feb. 27, 2015 (JP) ............................ JP2015-038916
Sep. 30, 2015 (JP) ............................ JP2015-193590

(51) Int. Cl.
G01N 33/53  (2006.01)
B01L 3/00  (2006.01)
(Continued)

(52) U.S. Cl.
CPC .... *G01N 33/5302* (2013.01); *B01L 3/502761* (2013.01); *G01N 33/54313* (2013.01);
(Continued)

(58) Field of Classification Search
CPC .... G01N 33/80; G01N 33/49; G01N 33/5302; G01N 33/54313; G01N 33/56966;
(Continued)

(56) References Cited

U.S. PATENT DOCUMENTS 7,735,652 B2  6/2010 Inglis et al.
9,956,562 B2 †  5/2018 Huang
(Continued)

FOREIGN PATENT DOCUMENTS

CN  102360010 A  2/2012
CN  103341372  10/2013
(Continued)

OTHER PUBLICATIONS

Second Chinese Office Action, dated Mar. 20, 2020, Chinese Application No. 201680012212.9, with translation, 15 pages.
(Continued)

*Primary Examiner* — Gailene Gabel
(74) *Attorney, Agent, or Firm* — Squire Patton Boggs (US) LLP

(57) ABSTRACT

The present invention relates to a method for applying a principle of Deterministic Lateral Displacement (DLD), and for separating cells depending on the particle sizes on the basis of the DLD principle after capturing targeted cells or untargeted cells on a carrier and thereby increasing particle sizes.

7 Claims, 30 Drawing Sheets

(51) Int. Cl.
*G01N 33/569* (2006.01)
*G01N 33/543* (2006.01)

(52) U.S. Cl.
CPC ............. *G01N 33/56966* (2013.01); *B01L 2200/0652* (2013.01); *B01L 2300/0816* (2013.01); *B01L 2300/0877* (2013.01); *B01L 2400/086* (2013.01)

(58) Field of Classification Search
CPC ......... B01L 3/502761; B01L 2400/086; B01J 19/0093; C12M 47/04; C12N 1/02; C12N 5/06; C12Q 1/04; C12Q 1/24
See application file for complete search history.

(56) References Cited

U.S. PATENT DOCUMENTS

| 2007/0026381 | A1 | 2/2007 | Huang et al. | |
|---|---|---|---|---|
| 2007/0190653 | A1* | 8/2007 | Heinrich | G01N 33/5002 435/345 |
| 2009/0215088 | A1 | 8/2009 | Forsyth et al. | |
| 2014/0227777 | A1 | 8/2014 | Choi et al. | |
| 2016/0047735 | A1* | 2/2016 | Grisham | B01L 3/502776 435/7.1 |

FOREIGN PATENT DOCUMENTS

| JP | 2005-204781 | 8/2005 |
|---|---|---|
| JP | 2007-519896 | 7/2007 |
| JP | 2008-507956 | 3/2008 |
| JP | 2010-213820 | 9/2010 |
| JP | 2013-501924 | 1/2013 |
| JP | 2013-142540 | 7/2013 |
| WO | 2008/124589 A2 | 10/2008 |
| WO | WO 2009/097247 | 8/2009 |
| WO | WO 2011/111740 | 9/2011 |
| WO | WO 2014/145152 | 9/2014 |

OTHER PUBLICATIONS

McGrath et al., "Deterministic lateral displacement for particle separation: a review", Lab Chip. Sep. 2014; 14(21): 4139-4158.
Extended European Search Report dated Jan. 19, 2018, in European Patent Application No. 16755023.5, 10 pages.
Inglis et al., "Critical particle size for fractionation by deterministic lateral displacement", Lab Chip. May 2006; 6(5): 655-658. Epub Mar. 17, 2006.
Liu et al., "Rapid isolation of cancer cells using microfluidic deterministic lateral displacement structure", Biomicrofluidics. Jan. 2013; 7(1): 011801-1-011801-10. Epub Jan. 7, 2013.
Loutherback et al., "Deterministic separation of cancer cells from blood at 10 mL/min", AIP Adv. Dec. 2012; 2(4): 042107-1-042107-7. Epub Oct. 3, 2012.
Okano et al., "Screening of Circulating Tumor Cells in Tumor-Bearing Mouse Blood by a Deterministic Lateral Displacement Micro Fluidic Device", 17th International Conference on Miniaturized Systems for Chemistry and Life Sciences, Oct. 27-31, 2013, Freiburg, Germany, 1021-1023.
International Search Report dated May 31, 2016, in International Patent Application No. PCT/JP2016/001055, 6 pages.
International Preliminary Report on Patentability dated Sep. 8, 2017, in International Patent Application No. PCT/JP2016/001055, 16 pages.

\* cited by examiner
† cited by third party

METHOD FOR SEPARATING CELLS, AND DEVICE THEREFOR

TECHNICAL FIELD

The present invention relates to a method for selectively separating a cell group having specific surface characteristics from among a plurality of cell groups each having different surface characteristics. In addition, the present invention relates to a method for removing minute aggregates in a cell suspension containing cells such as blood, and a device including this minute aggregate-removing structure, as well as a device including a cell-separating portion.

BACKGROUND ART

Separation of specific cells from a humoral mixed sample (e.g. blood or culture medium) is a technique required for basic study, diagnosis and treatment. Generally, the technique is known to be useful for separating cells having specific densities (specific gravity) (e.g. white blood cells and red blood cells) by centrifugation or the like. Other than that, methods such as a flow cytometry method and a magnetic separation method have been proved to be useful for this purpose, and as described in Patent Literature 1, a method for separating cells from a humoral mixed sample depending on their sizes by a filter structure is also known. Furthermore, as described in Patent Literature 2, a method for separating cells depending on their sizes by the use of a fluid device using a principle referred to as Deterministic Lateral Displacement (DLD) is also known.

However, in the separation methods described in Patent Literatures 1 and 2, it is difficult to separate the cells the kinds of which are different but whose sizes are similar to each other, since the methods are intended to separate cells from the humoral mixed sample depending on sizes of the cells themselves. In addition, in the separation method described in Patent Literature 3, a separation method in which cells are formed as a composite particle and then a sieve membrane is utilized is used, but in a case where such a separation method is used, there are problems that the processing has troubles such as an accompanying washing step, loss of cells, or the like, and thus a rapid, convenient and highly accurate separation and purification method is required. In addition to this, methods such as in Patent Literatures 4 to 6 have been proposed.

Furthermore, there has been also attempted the separation of cells in blood depending on their sizes or the like. However, the separation of circulating tumor cells (CTC) in blood has been difficult by a method based on the aforementioned DLD principle, because its size was similar to each size of white blood cells (10 to 20 µm).

Moreover, in the separation methods described in Patent Literatures 1 and 2, clogging is generated at a basic principle portion for separation due to the influence of minute aggregates existing in the sample, and thus there are some cases where the accuracy of separation is lowered or separation is made impossible.

Minute aggregates can be produced by aggregation of fibrin, other denatured proteins, fats and the like. In addition, each of the minute aggregates has a size ranging from a size equal to each blood cell such as leucocyte to a size larger than 200 µm, and is characteristically viscous. These minute aggregates are also present in fresh samples immediately after sampling, and a trend is that the longer the storage period is and the lower the storage temperature is, the larger the number and each size of the minute aggregates become. Furthermore, the minute aggregates are characteristically present even in a sample obtained by mixing with an anticoagulant and the like during sampling.

Accordingly, in a case where a known cell-separating treatment is executed without removing these minute aggregates, clogging may be generated on a part of the device due to the minute aggregates, resulting in lowering accuracy of the separation of the targeted cell and making processing itself difficult.

In contrast, minute aggregate-removing methods using a minute aggregate-removing filter as disclosed in Patent Literatures 7 and 8 are disclosed. However, although a large amount of samples can be treated in these methods, the targeted cells are lost, and thus the methods are unsuitable for separating rare cells in the sample without loss. Furthermore, in a filtration removal method using a commercially available nylon mesh filter, there is a case where the targeted cells can be lost, and minute aggregates cannot be completely removed.

CITATION LIST

Patent Literature

PTL 1: WO 2009/097247
PTL 2: U.S. Pat. No. 7,735,652
PTL 3: Japanese Patent Laid-Open No. 2008-507956
PTL 4: WO 2011/111740
PTL 5: Japanese Patent Laid-Open No. 2013-501924
PTL 6: Japanese Patent Laid-Open No. 2013-142540
PTL 7: Japanese Patent Laid-Open No. 2010-213820
PTL 8: Japanese Patent Laid-Open No. 2005-204781

Non Patent Literature

NPL 1: D. W. Inglis, et al, Critical particle size for fractionation by deterministic lateral displacement, Lab on a Chip, 6, 655-658 (2006)

SUMMARY OF INVENTION

Technical Problem

The object of the present invention is to provide a method for accurately, quickly and conveniently separating cells that are difficult to separate depending on sizes due to similar sizes of the cells, by utilizing a difference in the surface characteristics of the cells. Furthermore, the object of the present invention is to provide a method used for pretreatment in accurately fractionating the contained targeted cell from a cell suspension containing cells such as blood, wherein, in the subsequent cell-separating step, the targeted cells can be more accurately fractionated by removal, without loss, of the targeted cell in the sample and by removal, with high precision, of the minute aggregates in the sample, and to provide a device therefor.

Solution to Problem

One aspect of the present invention relates to a method in which, by applying the principle of Deterministic Lateral Displacement (DLD), the particle sizes are increased by capturing targeted cells or untargeted cells on a carrier, and then the cells are separated depending on particle sizes on the basis of the DLD principle.

First, the first aspect of the present invention is a method for separating cells depending on sizes from a cell suspension containing two or more kinds of cells, which are targeted cells and untargeted cells, in a continuous fluid flow, the method including the steps of:

adding a target-capturing substance that recognizes a characteristic structure on cell surfaces of the targeted cells to the cell suspension to thereby produce complexes of the targeted cells and the target-capturing substance, introducing the cell suspension containing the complexes into a cell-separating device including a separation area having a DLD microchannel structure, wherein a buffer is added and allowed to flow into a buffer inlet of the cell-separating device, and the cell suspension is added and allowed to flow into a sample inlet and to pass through a plurality of separation areas of the cell-separating device, separating complexes having sizes not smaller than a determined threshold from the cell suspension, wherein cells having sizes smaller than the threshold move together with the cell suspension flow, and the complexes having the sizes not smaller than the threshold are obliquely displaced to move relative to the flow, thereby being separated, and recovering the separated complexes from the outlet.

In addition, the second aspect of the present invention is a method for separating cells depending on sizes from a cell suspension containing two or more kinds of cells, which are targeted cells and untargeted cells, in a continuous fluid flow, the method including the steps of:

adding a target-capturing substance that recognizes a characteristic structure on cell surfaces of the untargeted cells to the cell suspension to thereby produce complexes of the untargeted cells and the target-capturing substance, introducing the cell suspension containing the complexes into a cell-separating device including a separation area having a DLD microchannel structure, wherein a buffer is added and allowed to flow into a buffer inlet of the cell-separating device, and the cell suspension is added and allowed to flow into a sample inlet and to pass through a plurality of separation areas of the cell-separating device, separating complexes having sizes not smaller than a determined threshold from the cell suspension, wherein cells having sizes smaller than the threshold move together with the cell suspension flow, and the complexes having the sizes not smaller than the threshold are obliquely displaced to move relative to the flow, thereby being separated, and recovering the separated targeted cells from the outlet.

Furthermore, in the present invention, the target-capturing substance is preferably composed of a combination body of a target-capturing molecule that recognizes the characteristic structure on the cell surfaces of the targeted cells or the untargeted cells and a substance carrying the target-capturing molecule, the target-capturing molecule is preferably an antibody, a peptide aptamer, a lectin, an intercellular adhesion molecule, a sugar chain or a cell-recognizable polymer, and the substance carrying the target-capturing molecule is preferably polystyrene or a latex.

In addition, in the present invention, the determined threshold is preferably 20 to 60 µm, and more preferably 30 to 50 µm. Moreover, in the present invention, the cell suspension is preferably blood, and the targeted cells are preferably tumor cells, more preferably circulating tumor cells or epithelial tumor cells.

In addition, another aspect of the present invention is a method for removing minute aggregates from a cell suspension containing targeted cells and minute aggregates in a continuous fluid flow, wherein the cell suspension or a liquid mixture of the cell suspension and a buffer solution is allowed to flow into a minute aggregate-removing device including a removal structure having a second microchannel structure and to pass through the microchannel in the minute aggregate-removing device, thereby capturing the minute aggregates. The method for removing the minute aggregates is useful as a method for removing the minute aggregates in a cell suspension (blood or the like) containing the minute aggregates. In addition, the method for removing the minute aggregates is combined with the aforementioned cell-separating method to thereby be used, and thus there can be obtained the method for more appropriately separating cells.

The targeted cells may contain complexes of the targeted cells and the carrier substance. In addition, the second microchannel structure is preferably composed of pillars arranged at intervals wider than 30 µm. Furthermore, in a case of separating the targeted cells from a cell suspension containing minute aggregates (for example, in a case of separating circulating tumor cells [CTC] from blood), the arrangement interval of the pillars in the second microchannel structure may be set to, for example, 80 to 250 µm, preferably 100 to 230 µm, and more preferably 120 to 220 µm, in a case where the cells are used in combination with the separation method.

In addition, the cell suspension is preferably blood, more preferably this blood is added with an anticoagulant reagent, further more preferably the anticoagulant is a thrombin inhibitor, and particularly preferably the thrombin inhibitor is PPACK.

Furthermore, another aspect of the present invention is a minute aggregate-removing device including a removal structure having a second microchannel structure, wherein the second microchannel structure is composed of pillars arranged at intervals wider than 30 µm and has a sample inlet at the front of the second microchannel and a sample outlet at the back of the microchannel. This second microchannel structure is preferably composed of two separate microchannel structure portions, and the minute aggregate-removing device preferably has a portion that converges the width of the flow in a middle between the two separate microchannel structure portions.

Moreover, another aspect of the present invention is an integrated cell-separating device continuously including a minute aggregate-removing portion having the second microchannel structure and a cell-separating portion separating the cells, wherein the second microchannel structure is composed of pillars arranged at intervals wider than 30 µm, and has a sample inlet at the front of the second microchannel structure and a sample outlet at the back of the cell-separating portion, and the cell-separating portion is continuously provided at the back of the minute aggregate-removing portion. The device is preferably an integrated cell-separating device, wherein the cell-separating portion is a separation structure according to size fractionation based on Deterministic Lateral Displacement (DLD).

Advantageous Effects of Invention

According to the present invention, there can be accurately, quickly and conveniently separated cells that are difficult to separate depending on the difference in sizes of cells themselves as compared with the prior art. In addition, according to the method of the present invention, it is also possible to reduce damage to the cells themselves and to accurately and selectively separate the targeted cells, by generating a large difference in sizes between the targeted cells introduced to the channel and the untargeted cells and thereby separating the targeted cells from the untargeted cells. Furthermore, in a case of separating the targeted cells, it is possible to separate the targeted cells by a channel having a simple structure without complicated devices and processes.

Moreover, according to the present invention, it is possible to accurately remove the contained minute aggregates without loss of the targeted cells, as compared with the prior art. In addition, according to the present invention, in a method using the cell-separating device, it is possible to accurately separate the targeted cells after removing the minute aggregates, by adopting a serial integrated channel structure. Furthermore, in a case of using the integrated cell-separating device of the present invention, it is possible to prevent clogging during fluid feeding and to separate and treat the cells from a relatively large amount of solution, as compared with a device without the minute aggregate-removing structure.

DESCRIPTION OF EMBODIMENTS

1. Principle for Separating Cells of the Present Invention

The present invention relates to a method for applying the principle of Deterministic Lateral Displacement (DLD), and for separating the cells depending on the particle sizes on the basis of the DLD principle after capturing targeted cells or untargeted cells on a carrier and thereby increasing particle sizes.

Figure 1:
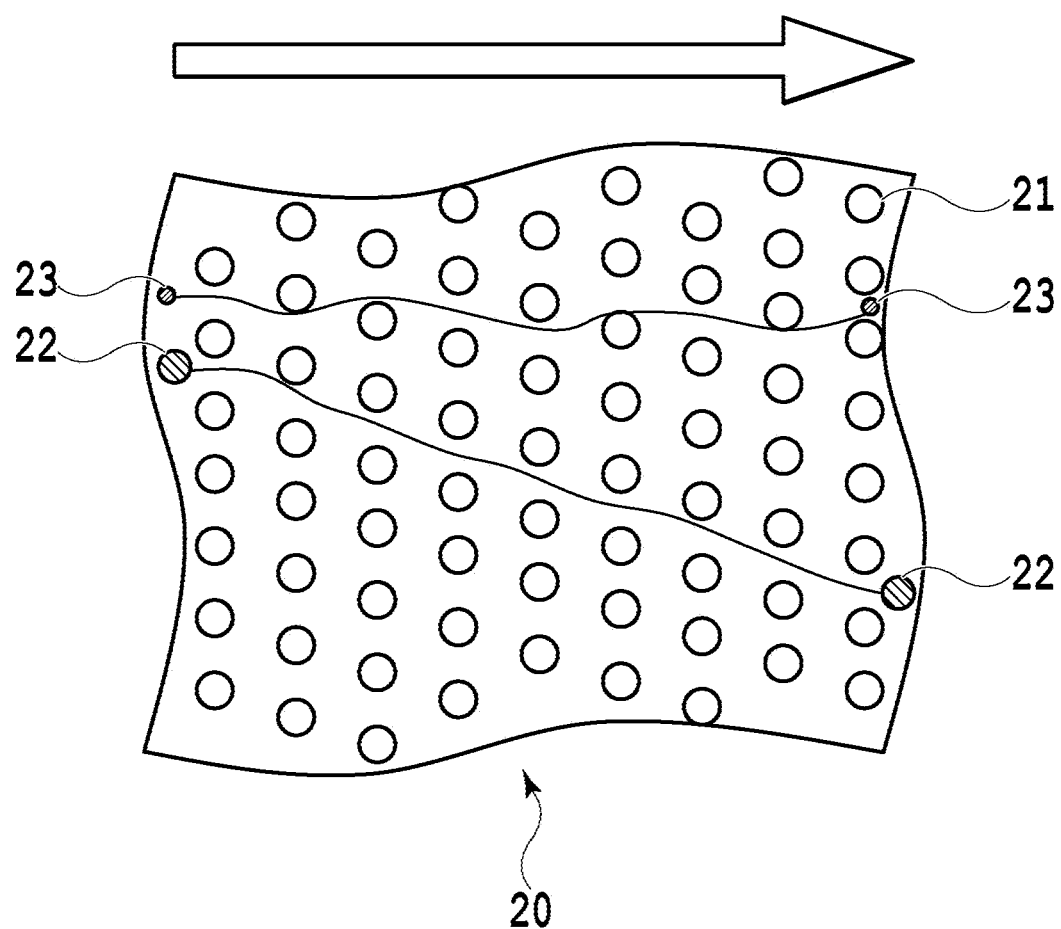
FIG. 1 is a schematic view explaining a basic principle of the separation method related to an embodiment of the present invention.

FIG. 1 is a schematic view explaining a basic principle of the separation method related to the embodiment of the present invention. A method referred to as Deterministic Lateral Displacement (DLD) is used as the basic principle of separation.

1-1. Deterministic Lateral Displacement (DLD)

Deterministic Lateral Displacement (DLD) is a method for achieving sorting depending on sizes by utilization of a property in which, in a case where a dispersion of particles is allowed to flow through slightly-deviated pillar structures, large particles obliquely flow by change of the flow caused around the pillars, whereas small particles proceed globally in a linear manner along a laminar flow (see Non-Patent Literature 1, FIG. 1). In the method referred to as Deterministic Lateral Displacement using a channel in which obstacles (micropillars) are regularly arranged while being deviated, the small particles linearly proceed along the flow, whereas the large particles obliquely proceed along the deviation of the obstacles with the change of the flow caused around the obstacles.

Generally, this DLD principle is also applied to separation of cells, e.g. separation of blood components, red blood cells, while blood cells and CTCs. Larger cells can be selected through the DLD microchannel depending on the sizes of the cells, by allowing the blood cells to flow on a size-selecting micropost structure and to pass through a microfluidic device using DLD. However, since a tumor cell in blood has a cell size similar to that of white blood cells, it is difficult to divide and separate the both of them.

In the present invention, as described below, a target-capturing substance that recognizes a characteristic structure on cell surfaces of targeted cells or untargeted cells is added to a cell suspension to thereby produce a complex of the targeted cells or the untargeted cells and the target-capturing substance, and thus a difference in size is generated, and then the cells are separated by utilization of the cell-separating device having the basic structure of the DLD microchannel.

1-2. Threshold of Diameter of Obliquely Displaced Particle in DLD Principle, and Cell-Separating Device On the basis of the DLD principle described in Non-Patent Literature 1, a threshold (Dc) of the diameter of the obliquely displaced particle can be set by a particle size intended to be separated. More specifically, the set value of the threshold Dc can be calculated from the following formula.

$$Dc = 2\eta G \varepsilon \quad \text{Formula 1}$$

Dc: threshold of the diameter of the obliquely displaced particle
η: variable
G: inter-pillar gap
ε: deviation angle of the pillar (tan θ)

The following approximate Formula 2 can be obtained by solving the above Formula 1.

$$Dc = 1.4 G \varepsilon^{0.48} \quad \text{Formula 2}$$

In addition, since the separation is successful in a case of about $0.06 < \varepsilon < 0.1$ from the empirical rule, the following relational formula can be derived by using $\varepsilon = \tan \theta = 1/15 = 0.067$, $$G \approx 2.62057 Dc \quad \text{Formula 3}$$

In addition, from the above formulas, there can be produced a cell-separating device having a basic structure portion where the pillars (obstruction structures) with a specific inter-pillar gap are arranged by calculation of the inter-pillar gap G on the basis of the threshold Dc of the diameter of the obliquely displaced particle. In this way, a cell-separating device having a DLD microchannel with a targeted threshold Dc can be fabricated.

First, FIG. 1 shows a basic structure 20 of the DLD microchannel (separation area), in which there are provided obstacle structures 21 arranged obliquely relative to a flow method of the fluid toward the arrow direction according to a fixed rule. In the fluid toward the arrow direction, a change in the flow rate is generated in a peripheral portion of the obstacle structure 21. By utilization of the change in the flow rate due to the continuously arranged obstacle structures 21, the traveling direction of particles in the fluid can be changed in a size-dependent manner by the use of a certain size as a threshold.

In relation to the change in the traveling direction, a particle 22 not smaller than a certain size is obliquely displaced in accordance with the arrangement of the continuously arranged obstacle structures 21. On the other hand, a particle 23 smaller than a certain size (threshold) does not follow the behavior of the particle described above, but proceeds straight along the flow direction while bypassing the obstacle structures 21.

In this way, the particles can be separated in a direction perpendicular to the flow direction depending on sizes of particles for various purposes by designing an arrangement pattern of the obstacle structures 21 for which the setting of a threshold capable of separating the targeted size is performed, according to the known method (Non-Patent Literature 1). Furthermore, different recovering channels are provided on the downstream portion in the flow direction, and thus the separated particles can be individually recovered.

Note that the shape of the obstacle structures 21 is not limited to only the columnar structure as shown in the figure, but may be any polygonal columnar structure like, for example, triangle column as long as the shape can change the targeted flow rate.

Figure 2:
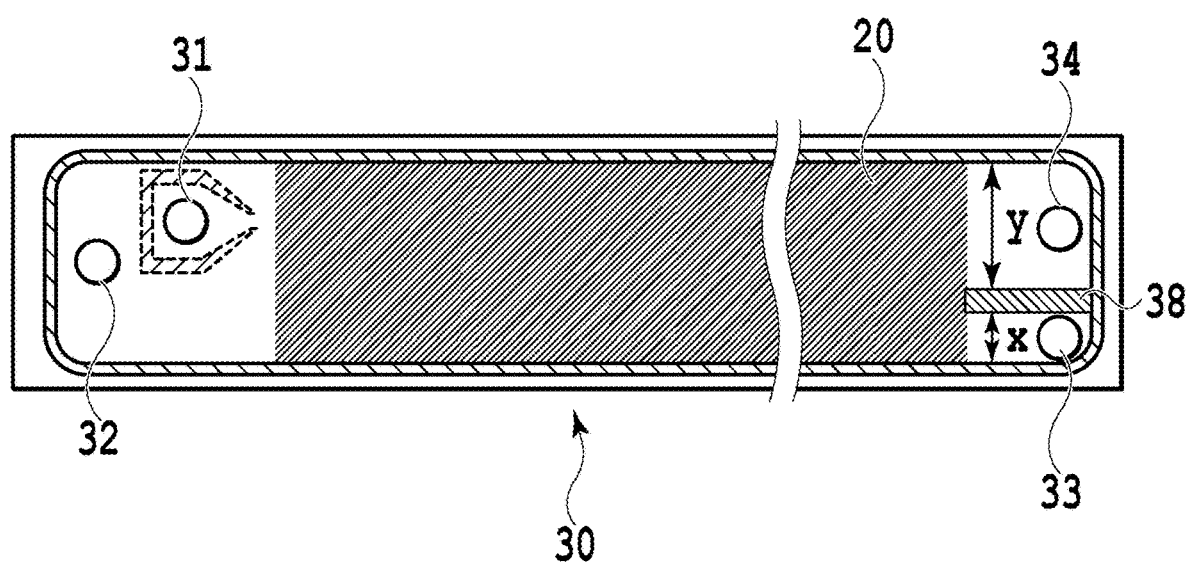
FIG. 2 is a schematic view explaining a separation device including a basic structure of a DLD microchannel (separation area) related to the embodiment of the present invention.

FIG. 2 is a schematic view explaining a cell-separating device 30 including a basic structure of the DLD microchannel related to the embodiment of the present invention. Hereinafter, the basic structure of the cell-separating device 30 will be explained with reference to a top view. First, a fluid inlet structure includes a sample inlet 31 and a buffer inlet 32.

In addition, the outlet structure of the fluid includes a first outlet 33 that discharges a fraction including particles not smaller than a threshold (a certain size) which have proceeded while being displaced in a direction according to the arrangement of the obliquely-arranged obstacle structure portion, and a second outlet 34 that discharges a fraction including particles smaller than a certain size which have proceeded straight along the flow direction. Note that the number of the first outlet 33 and the number of the second outlet 34 are not limited to only one, respectively, as shown in the schematic view, but may have a plurality of outlets, respectively, depending on to the purposes.

The basic structure 20 of the DLD microchannel having the micropillar structures is continuously arranged between the sample inlet 31 and the first outlet 33 and between the buffer inlet 32 and the second outlet 34 in the cell-separating device, and by this serial structure portion, the particles in the liquid mixture can be separated in a direction perpendicular to the flow direction in a size-dependent manner. Regarding the continuously arranged portions of the basic structure 20, the basic structures having the constantly same design may be continuously arranged, and areas where the designs are gradually changed can also be set depending on their purposes. One of or a combination of plural isotonic solutions may be used as a buffer solution in order to avoid the influence on the cells. For example, saline, PBS, or the like may be used.

Figure 18A:
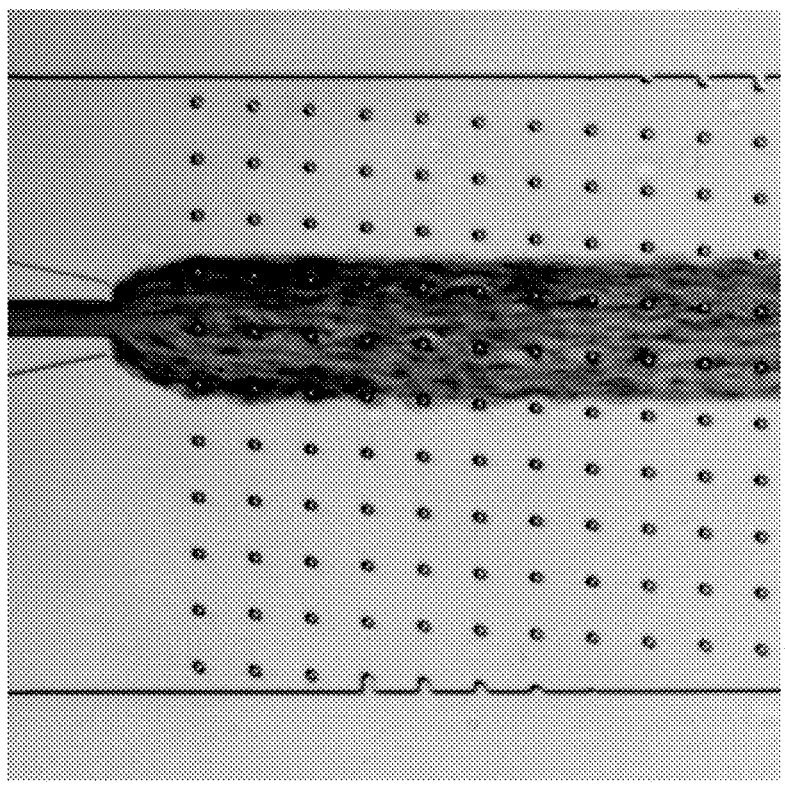
FIG. 18A is a view showing a state where clogging is eliminated in the separation device for explaining Examples of the present invention.
Figure 18B:
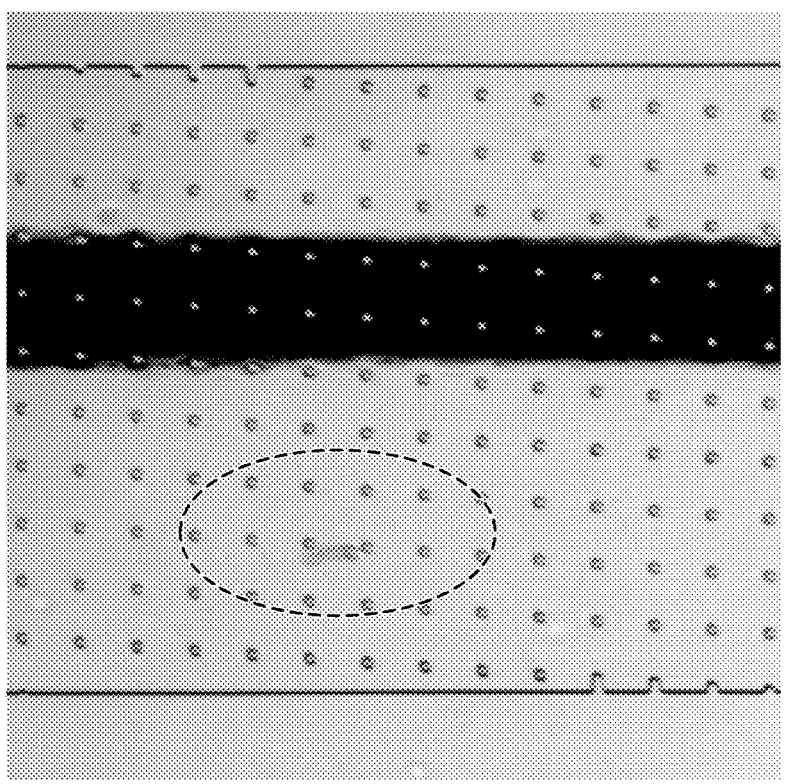
FIG. 18B is a view showing a state where clogging is eliminated in the separation device for explaining Examples of the present invention.

Regarding the structure of the entrance portion from the sample inlet 31 to the fluid device 30, it is preferable to provide a compartment structure having a constant width as shown in the figure since the liquid mixture is required to flow as described below. The liquid mixture fed from the sample inlet 31 flows as shown in, for example, FIG. 18A while maintaining the buffer solution fed from the buffer inlet 32 and a laminar flow (a flow forming a layer parallel to the flow direction), particles larger than a fixed threshold are obliquely displaced relative to the flow direction according to the aforementioned separation principle, and thereby the particles are separated from the liquid mixture layer as shown in FIG. 18B. On the other hand, particles smaller than a fixed threshold flow straight with the flow of the liquid mixture layer. In this way, for the purpose of separating cells, the position of the sample inlet 31 is required to be set close to the second outlet 34 side of the fluid device 30.

Figure 21:
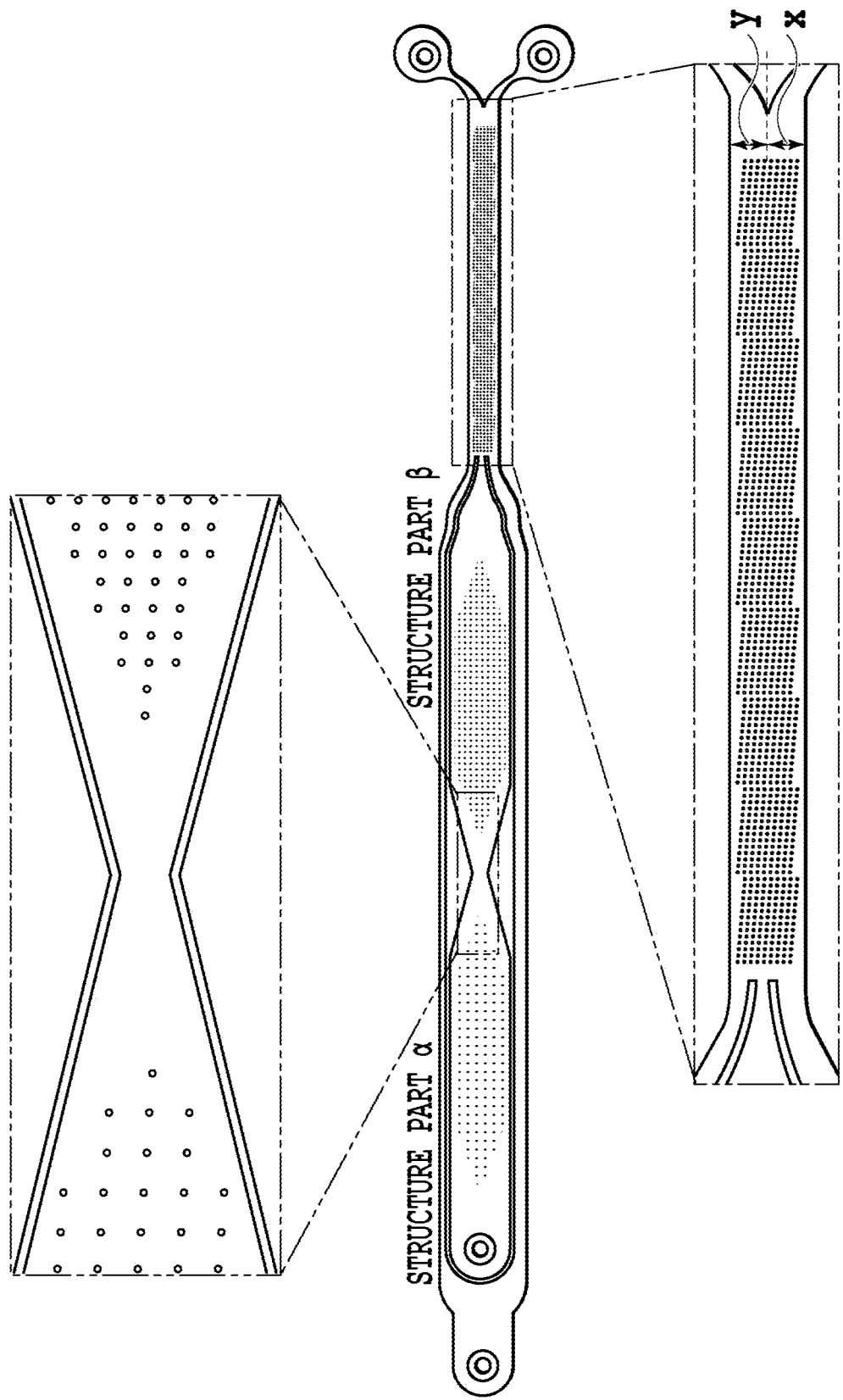
FIG. 21 is a plan view of the integrated cell-separating device, an enlarged view of a portion for converging a width of flow, and an enlarged view of the cell-separating portion.

In addition, the structures of the first outlet 33 and the second outlet 34 can be appropriately changed in the design depending on the purpose in order to adjust the amount of discharged fluid. For example, in a case where a compartment 38 in the vicinity of the outlet is provided so that the ratio between the upper portion and the lower portion in the figure is 1:1, the ratio between the amounts of the fluid obtained from the respective outlets is approximately 1:1. In contrast, in a case where the compartment 38 is similarly provided so that the ratio is 49:1, the amount of fluid obtained from the first outlet 33 can be concentrated by approximately 50 times. In this way, depending on the purpose, the compartment can also be used not only for separation of the particles in the liquid mixture but also for concentration of the fluid volume. For example, the separation and the concentration can be achieved by setting the ratio between y and x shown in the compartment 38 in FIG. 2 and a branch portion 39 in FIG. 21 to 1:1, 49:1 or the like.

Figure 3:
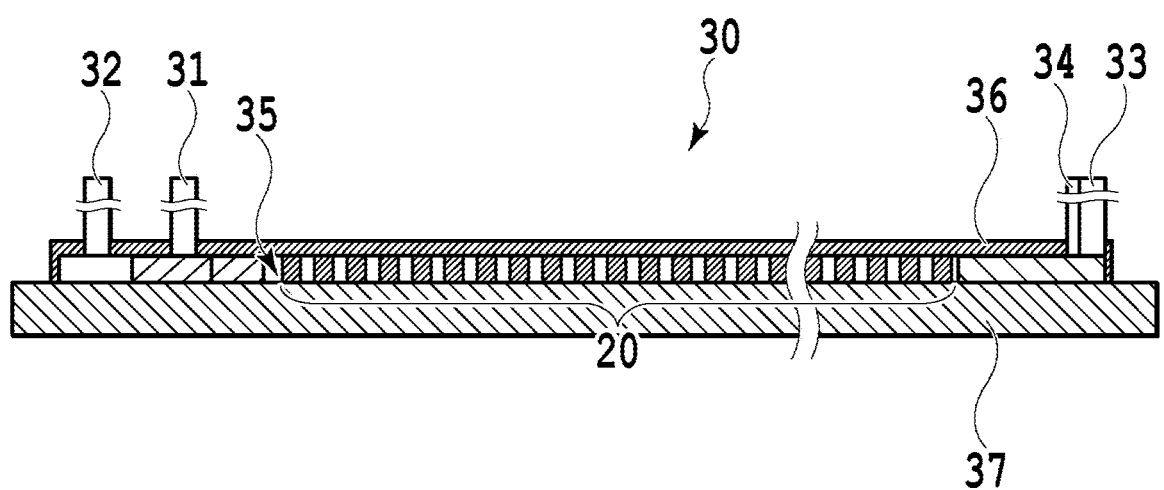
FIG. 3 is a vertical cross-sectional schematic view of the separation device including the basic structure of the DLD microchannel related to the embodiment of the present invention.

FIG. 3 is a vertical cross-sectional schematic view of the cell-separating device related to the embodiment of the present invention. The cell-separating device 30 is composed of the basic structure 20 of the DLD microchannel, and is fabricated by joining, with a flat structure portion 37, a channel structure portion 36 including each shape of the inlet, the outlet structure portion and the like, and has a channel space 35 in the space thereof. Furthermore, the basic structure 20 can also be used while Design change are appropriately made at each portion of the sample inlet 31, the buffer inlet 32, the first outlet 33 and the second outlet 34, by proper joining of tubes therewith and by provision of a joining portion with a syringe or the like.

The height of the channel space 35 is not particularly limited as long as it is set to a height allowing a complex 5 to pass, but it is desirable that the height is set to a height at which two or more complexes 5 cannot be simultaneously present in the height direction of the channel space 35 in order to perform accurate separation.

In the method for fabricating the members in the channel structure portion 36 and the channel structures, the members and the channel structures can be fabricated by optionally selecting any known method. There can be used, as materials for the members, for example, glass, silicone, dimethylpolysiloxane, plastic, and the like. In addition, the flat structure portion 37 is not particularly limited as long as the portion is flat and the material can be joined with the channel structure portion 36, but a strong glass, strong plastic or the like is preferably used.

Note that this cell-separating device 30 has each shape of the basic structure, the inlet and outlet structure portions and the like, and there is no problem as long as the channel space is formed, and for example, the structure can be a structure having each shape of the basic structure, the inlet and outlet structure portions and the like on the members on the side of the flat structure portion 37 shown in the figure.

Figure 4:
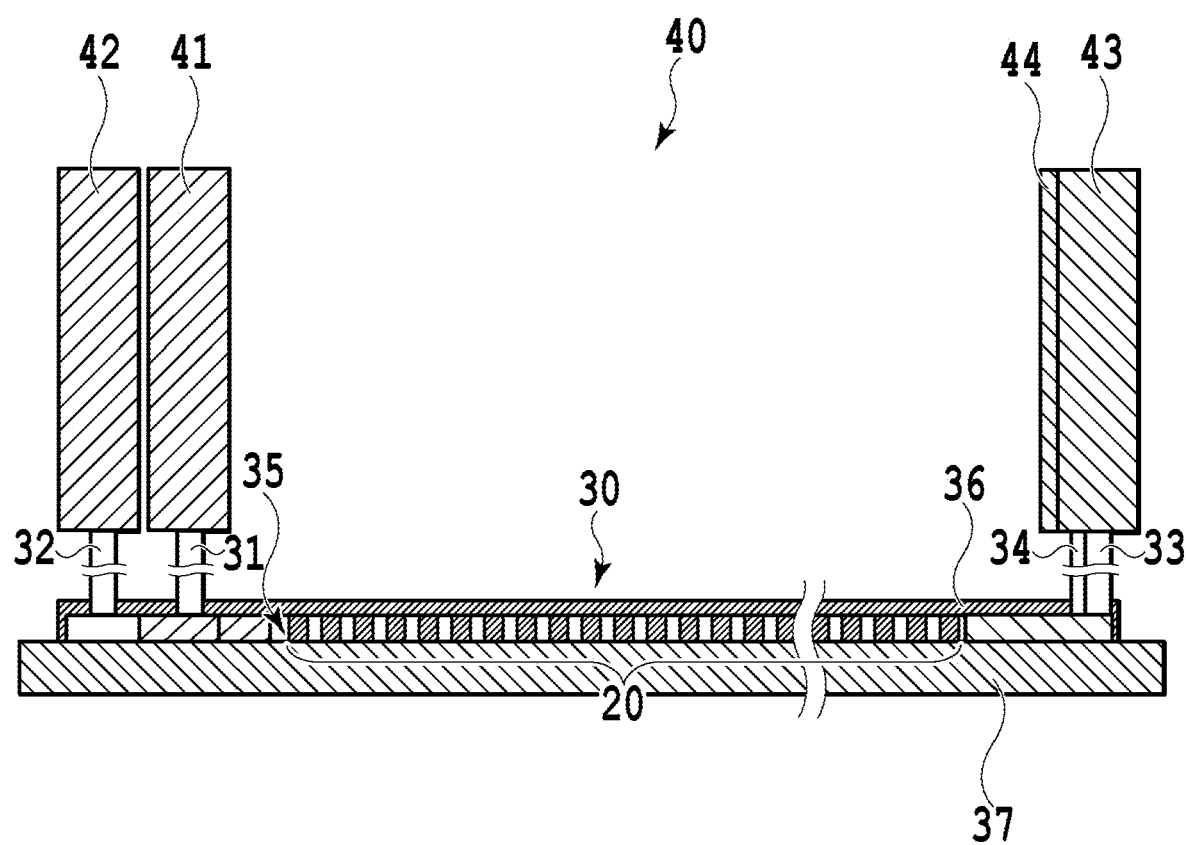
FIG. 4 is a schematic view explaining the separation device including a fluid feed portion and a recovery portion related to the embodiment of the present invention.

FIG. 4 is a schematic view explaining the separation device including a fluid feed portion and a recovery portion related to the embodiment of the present invention. In a separation device 40, the cell-separating device 30 having the basic structure of the DLD microchannel is provided with a sample fluid feed portion 41 and a buffer fluid feed portion 42 on the sample inlet 31 and the buffer inlet 32, respectively. In addition, the first outlet 33 is provided with a first recovery portion 43 and the second outlet 34 is provided with a second recovery portion 44.

Each of the sample fluid feed portion 41 and the buffer fluid feed portion 42 has a structure having a fluid feed system, and independent fluid feeding can be respectively carried out at a constant rate. These portions are not particularly limited as long as the structures can feed fluid at a constant rate, but fluid feeding through, for example, a syringe pump or the like is suitable. In addition, as necessary, the sample fluid feed portion 41 may include a stirring mechanism for preventing precipitation and aggregation of the complex 5, and an automation mechanism for adjusting a liquid mixture 4.

The first recovery portion 43 and the second recovery portion 44 are not particularly limited as long as they have structures capable of recovering an effluent, but may have structures or the like capable of fractionating an effluent immediately before and after the start of the separation.

2. Cell-Separating Method of the Present Invention

Hereinafter, the separation method of the present invention will be explained with reference to the figures.

The present invention is a method for separating cells depending on sizes in a continuous fluid flow in a cell suspension containing two or more kinds of cells including the targeted cells and the untargeted cells, as described above. Note that the "cell suspension" is not particularly limited as long as it contains two or more kinds of cells including the targeted cells and the untargeted cells, but it can be exemplified by body fluids such as blood, lymph, saliva, urine, and tear.

Figure 5:
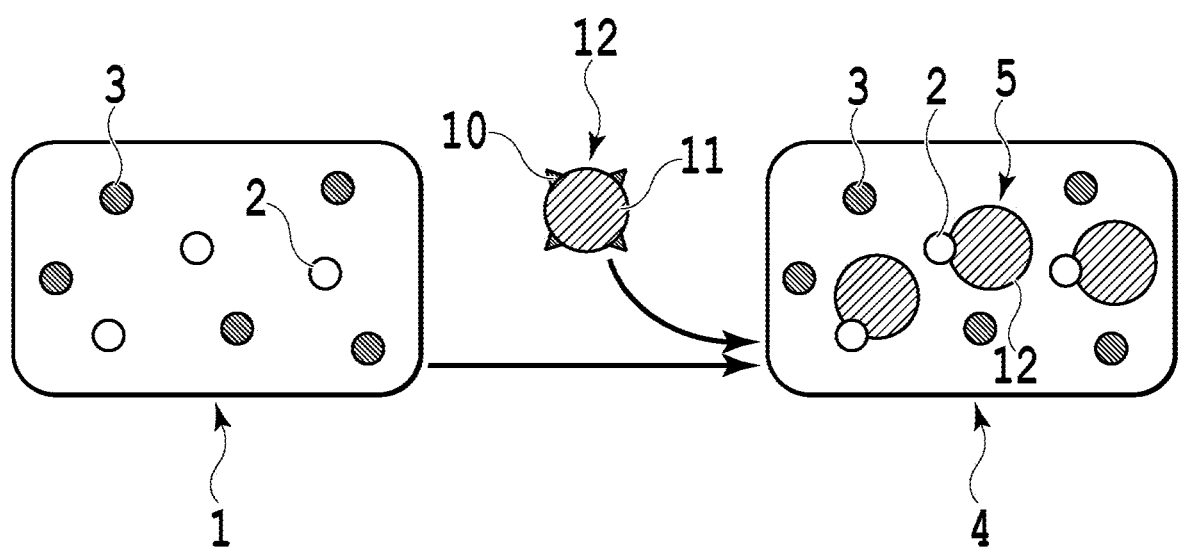
FIG. 5 is a schematic view explaining a cell-containing cell suspension and a target-capturing substance related to the embodiment of the present invention.

2-1. Step of Producing Complex of Targeted Cell or Untargeted Cell and Target-Capturing Substance FIG. 5 is a schematic view explaining the cell-containing cell suspension and the target-capturing substance related to the embodiment of the present invention. First, as to a cell suspension 1 containing a targeted cell 2 and an untargeted cell 3, a target-capturing substance 12 that is a combination body of a target-capturing molecule 10 recognizing a characteristic structure on a cell surface of the targeted cell and a substance 11 carrying the target-capturing molecule 10 is mixed in the cell suspension 1, and thus, in the resulting liquid mixture 4, the complex 5 of the targeted cell 2 and the target-capturing substance 12 is produced.

Note that the untargeted cell 3 contained in the cell suspension 1 is not limited to one kind, and in a case where the cell 3 is a cell which does not have a characteristic structure on the cell surface of the targeted cell recognized by the target-capturing molecule 10, its type and number are not limited. In addition, the target-capturing molecule 10 is not limited to one kind as long as it is a molecule that recognizes a characteristic structure on the cell surface of the targeted cell 2 and that does not recognize a characteristic structure on the cell surface of the cell other than the targeted cell 2, and a plurality of kinds and numbers required can also be appropriately selected for use.

More specifically, the target-capturing substance 12 may be produced by carrying the same or different kinds of plural target-capturing molecules 10 on the substance 11 carrying the target-capturing molecule 10. In addition, the substance 11 for carrying a plurality of target-capturing molecules 10 may carry the same or different kinds of target-capturing molecules 10, and the molecules can be appropriately selected in accordance with the intended use to thereby produce the target-capturing substance 12. Note that, in order to accurately obtain a targeted cell, a combination of plural target-capturing molecules 10 that satisfy the above-mentioned conditions is preferably used. Furthermore, a plurality of kinds of sizes can be properly used, in accordance with the intended use, also as the size of the substance 11 carrying the target-capturing molecule.

For example, in a case where each targeted cell 2 further has a characteristic structure a, b, . . . on the cell surface, a substance 11a including a target-capturing molecule 10a, a substance 11b including a target-capturing molecule 10b, . . . are used respectively, and the substances are allowed to pass through a plurality of separation threshold areas in the subsequent separation step by utilization of the difference in sizes among the substance 11a carrying the target-capturing molecule, the substance 11b carrying the target-capturing molecule, . . . , and thereby the targeted cell having each characteristic structure of a, b, . . . can also be separated into each outlet and recovered.

In addition, depending on the intended use, the untargeted cell can also be removed by production and separation of a conjugate particle of the untargeted cell 3 and the target-capturing molecule.

More specifically, the complex 5 of the untargeted cell 3 and the target-capturing substance 12 can be produced in the liquid mixture 4 by addition of the target-capturing substance 12 which is a combination of the target-capturing molecule 10 that recognizes a characteristic structure on the surface of the untargeted cell and the substance 11 carrying the target-capturing molecule 10, to the cell suspension 1 containing the targeted cell 2 and the untargeted cell 3 (not shown).

Note that, in a similar way to this case, the target-capturing molecule 10 is not limited to one kind as long as it is a molecule that recognizes a characteristic structure on the surface of the untargeted cell and that does not recognize a characteristic structure on the cell surface of the targeted cell 2, and a plurality of kinds and numbers required can be appropriately selected for use.

The target-capturing molecule 10 is not particularly limited as long as it is a molecule that recognizes a characteristic structure on the cell surface of the cell producing the complex 5 and that does not recognize a characteristic structure on the cell surfaces of other cells. There can be appropriately used, as the target-capturing molecule 10, for example, any of an antibody, a peptide aptamer, a lectin, an intercellular adhesion molecule, a sugar chain and other cell-recognizable polymers, etc., or a combination of plural types of them.

The substance 11 carrying the target-capturing molecule can use a member made of a metal, an inorganic material, and a polymer such as resin. This member may be made of a single material, or may be used by the combination of plural kinds. In a case where the plural kinds of materials are used, it is preferable to use a member formed so that each component is uniformly kneaded. In addition, a high molecular polymer may be selected as a material of the substance 11 carrying the target-capturing molecule, and specifically, polystyrene, latex, or the like can be used as the material.

As long as the substance 11 carrying the target-capturing molecule is made of the above-mentioned materials, the member is not particularly limited, but since the member is an important factor in the subsequent separation step, it is preferable to use the member having a uniform specific gravity. Furthermore, in a case where the specific gravity is low during a reaction in the cell suspension 1, dispersion in the cell suspension may not be uniform, and thus a member having a specific gravity close to or slightly higher than that of water is preferably selected.

The target-capturing substance 12 is a combination body of the target-capturing molecule 10 and the substance 11 carrying the target-capturing molecule 10 as described above. The target-capturing molecule 10 and the substance 11 carrying it can be bound to each other by a known method. It is possible to use a physical adsorption method, a chemical bonding method, or the like in order to, for example, immobilize an antibody as a target-capturing molecule on the substance 11. In the case of the chemical bond, for example, in a case where the substance is made of a material containing a hydroxyl group on its surface, a carboxyl group in an antibody is active-esterified, and then the hydroxyl group is caused to react with this ester group, with the result that the antibody can be immobilized on the surface. Furthermore, it is also possible to use a binding method via Protein A or Protein G. Note that it is also possible to use a commercially available substance e.g. beads that carry an antibody purchased, as the target-capturing substance 12.

The size of the target-capturing substance 12 is required to be selected so that the size of the complex 5 is larger than each size of other cells to be distinguished and is a distinguishable size. For example, in a case where the complex 5 of the targeted cell 2 and the target-capturing substance 12 is formed and is separated from the untargeted cell 3, the size of the complex 5 has to be larger than that of the untargeted cell 3.

More specifically, in a case where the diameter of the targeted cell 2 is 10 to 14 μm and the diameter of the untargeted cell 3 is 8 to 12 μm, the diameter of the target-capturing substance is required to be at least no smaller than 2 μm, preferably the diameter is not smaller than 5 μm for more accurate separation, and preferably a substance having a further larger diameter is used as long as the diameter does not cause trouble to the subsequent experiment. In addition, in light of the cell-separating device based on the DLD principle, the sizes of ordinary cells, or the like, more specifically the size of the target-capturing substance 12 is 7 μm to 60 μm, preferably 15 μm to 50 μm, more preferably 20 μm to 40 μm. In particular, since the size of the circulating tumor cell (CTC) in the blood is similar to that of the white blood cell (10 to 20 μm), the target-capturing substance having a diameter of 20 μm to 40 μm is preferably used in separating the circulating tumor cell from the blood.

2-2. Step of Separating Complex by Use of Cell-Separating Device

The present invention include: a step of introducing the cell suspension containing the complexes into a cell-separating device including a separation area having a DLD microchannel structure, wherein a buffer is added and allowed to flow into a buffer inlet of the cell-separating device, and the cell suspension is added and allowed to flow into a sample inlet and to pass through a plurality of separation areas of the cell-separating device; and a step of separating complexes having sizes not smaller than a determined threshold from the cell suspension, wherein cells having sizes smaller than the threshold move together with the cell suspension flow, and the complexes having the sizes not smaller than the threshold are obliquely displaced to move relative to the flow, thereby being separated.

2-2-1. Step of Producing Complex with Targeted Cell for Separation

First, in the first aspect of the present invention, a complex with the targeted cell is produced, and then the cell-separating device including a separation area having the DLD microchannel structure is used to separate a complex having a size not smaller than a determined threshold.

Figure 6:
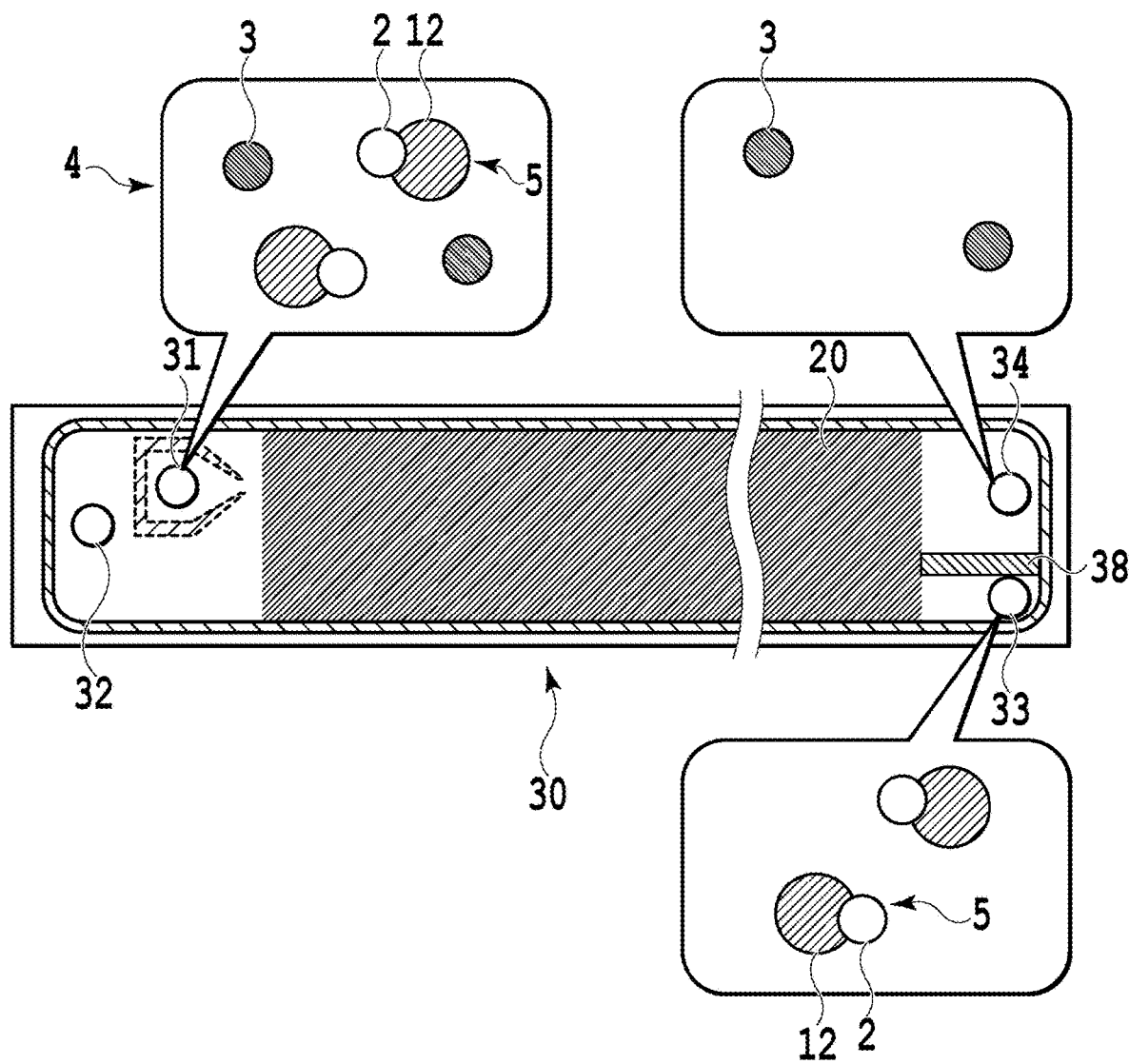
FIG. 6 is a schematic view explaining the separation method for capturing targeted cells related to the embodiment of the present invention.

FIG. 6 is a schematic view explaining the separation method for capturing the targeted cell related to the embodiment of the present invention. In this method, first, the target-capturing substance 12 that recognizes a characteristic structure on the cell surface of the targeted cell is mixed in a cell suspension containing the targeted cell 2 and the untargeted cell 3, and thus the complex 5 of the targeted cell 2 and the target-capturing substance 12 is formed.

Next, as to the cell-separating device 30 prepared so that the channel space portion has been previously filled with a buffer to remove bubbles, the liquid mixture 4 containing the untargeted cell 3 and the complex 5 is introduced from the sample inlet 31 into the cell-separating device 30, and at the same time, the buffer is continuously introduced from the buffer inlet 32. Thereafter, in the cell-separating device 30, the untargeted cell 3 proceeds straight by the basic structure 20 (separation area) having the DLD microchannel structures continuously arranged in the cell-separating device 30, whereas the complex 5 is obliquely displaced to move relative to the flow, thereby being separated. As a result, the composite particle 5 containing the targeted cell 2 is obtained from the first outlet 33, and the untargeted cell 3 is obtained from the second outlet 34. As described above, cell separation can be performed.

In the present invention, a complex with a targeted cell is formed in the first step, and then a complex having a size not smaller than the determined threshold is separated. In this case, although the threshold depends on the size of the complex, an appropriate range can be selected from the relationship with the size of the complex, the size of the target-capturing substance, the targeted cell, and the size of the untargeted cell to be distinguished, and the like.

For example, in a case of assuming a case of use for the separation of cells in blood, the size of the red blood cell is 6 to 8 μm, while the size of the white blood cell is comparatively large, 9 to 15 μm, and the size of the circulating tumor cell (CTC) that can be present in blood is approximately 10 to 20 μm, and thus, in light of separation from the white blood cell, the threshold is preferably no smaller than 20 μm, more preferably no smaller than 30 μm for separation from the white blood cell as the untargeted cell. On the other hand, for separation with high accuracy, a target-capturing substance of a relatively large size is preferably used, and the size of the target-capturing substance is preferably 15 μm to 50 μm, more preferably 20 μm to 40 μm, as described above. Accordingly, for example, in a case where a target-capturing substance having a size of 30 μm is used, it can be assumed that the size of the complex with the circulating tumor cell (CTC) as the targeted cell is about 40 to 50 μm. In addition, in a case where a target-capturing substance with a preferable size ranging from 20 μm to 40 μm is used, it can be assumed that the size of the complex is 30 μm to 60 μm. Taken together, for easily and accurately separating the targeted cell, it is preferable that a threshold to be determined is not smaller than the size of the untargeted cell to be distinguished, and not larger than the upper limit of the complex size expected from the sizes of the targeted cell and the target-capturing substance. Specifically, the threshold Dc to be determined is set to preferably 20 to 60 μm, and more preferably 30 to 50 μm.

Note that, since the range of the threshold Dc varies depending on the sizes of the target-capturing substance, the targeted cell, the untargeted cell and the complex, the range can be determined by appropriate selection of the targeted cell, the untargeted cell and the target-capturing substance.

2-2-2. Step of Producing Complex with Untargeted Cell for Separation

In the second aspect of the present invention, a complex with an untargeted cell is produced, then a cell-separating device including a separation area having a DLD microchannel structure is used to separate a complex having a size not smaller than the determined threshold.

Figure 7:
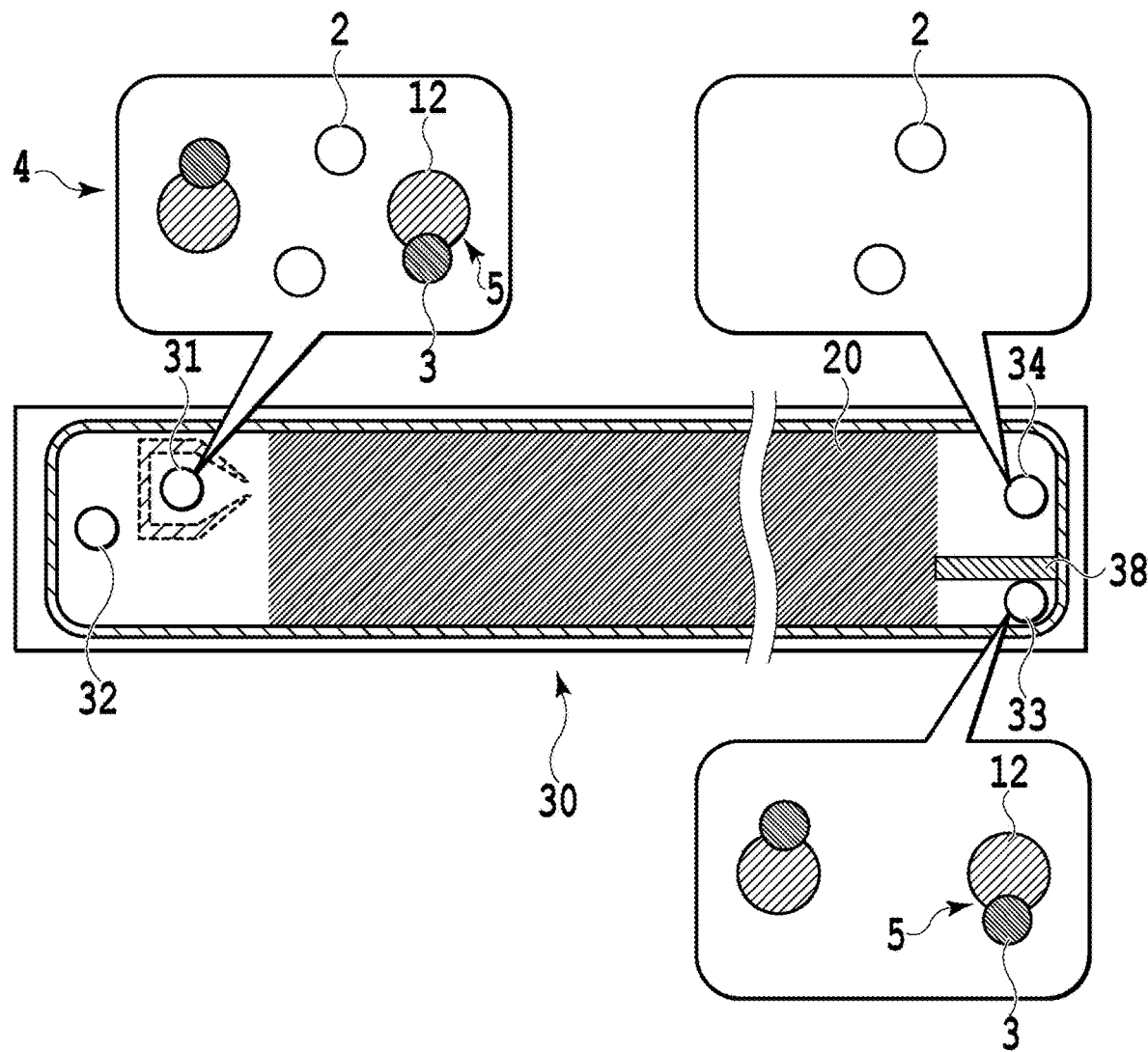
FIG. 7 is a schematic view explaining the separation method for capturing untargeted cells related to the embodiment of the present invention.

FIG. 7 is a schematic view explaining the separation method for capturing the untargeted cell related to the embodiment of the present invention. In contrast to the aforementioned method, in this method, first, the target-capturing substance 12 that recognizes a characteristic structure on the cell surface of the untargeted cell is mixed in a cell suspension containing the targeted cell 2 and the untargeted cell 3 to form the complex 5 of the untargeted cell 3 and the target-capturing substance 12.

Next, in a similar way to the aforementioned method, for the cell-separating device 30 prepared so that the channel space portion is previously filled with a buffer to remove bubbles, the liquid mixture 4 containing the targeted cell 2 and the complex 5 is introduced from the sample inlet 31 into the cell-separating device 30, and at the same time, the buffer is continuously introduced from the buffer inlet 32. Thereafter, in the cell-separating device 30, the targeted cell 2 and the complex 5 are separated in a direction perpendicular to the flow direction by the basic structure 20 portion continuously provided in the cell-separating device 30. As a result, the complex 5 having the untargeted cell 3 is obtained from the first outlet 33, and the targeted cell 2 is obtained from the second outlet 34. As described above, cell separation can be performed.

The aforementioned two methods can be properly used depending on the purpose. For example, in a case where the target-capturing molecule 10 for the targeted cell 2 is clear and highly specific, the method described in FIG. 6 can be suitably used. On the other hand, in a case where the target-capturing molecule 10 for the targeted cell 2 is not clear, the method described in FIG. 7 can be used to separate the targeted cell 2. In addition, each technique can be properly used depending on the kind and the number of untargeted cells 3.

Furthermore, the aforementioned two methods can be properly used depending on the purpose after separation. For example, in a case where the targeted cell 2 is intended to be separated as it is without formation of the complex 5, the separation can be carried out by the method described in FIG. 7. Moreover, also in the case of being executed by the method described in FIG. 6, there can also be adopted a technique in which the complex 5 is dissociated by the use of any known method to be divided into the targeted cell 2 and the target-capturing substance 12 and furthermore only the targeted cell 2 is separated by the use of any known method, but the procedure is complicated, and thus, in this case, the procedure is preferably executed by the method described in FIG. 7.

2-3. Step of Recovery

The present invention includes a step of recovering a complex containing the separated targeted cell from the outlet, or a step of recovering the separated targeted cell from the outlet. In a case where a complex of the targeted cell and the target-capturing substance is produced as in the first aspect of the present invention, the complex is recovered from the outlet, and in a case where a complex of the untargeted cell and the target-capturing substance is produced as in the second aspect of the present invention, the targeted cell is recovered from the outlet. These recoveries can be appropriately carried out by using a known method such as attaching a tube to the outlet and performing suction through the pump.

2-4. Step of Removing Minute Aggregates

In the cell separation method of the present invention, in a case where the targeted cell is separated from a cell suspension containing minute aggregates such as blood, a step of removing the minute aggregates which will be described later is preferably added before the separation step. This step can also be carried out as a pretreatment for blood or the like, but in a case of being combined with the aforementioned cell separation method, the targeted cell can be effectively separated by provision of a step of removing the minute aggregates after the step of producing the complex with the blood or the like, and before a step of introducing the complex into the cell-separating device.

Another aspect of the present invention relates to a method of removing minute aggregates contained in blood or the like by a minute aggregate-removing device including a removal structure having a microchannel structure, and the minute aggregate-removing device.

Figure 10:
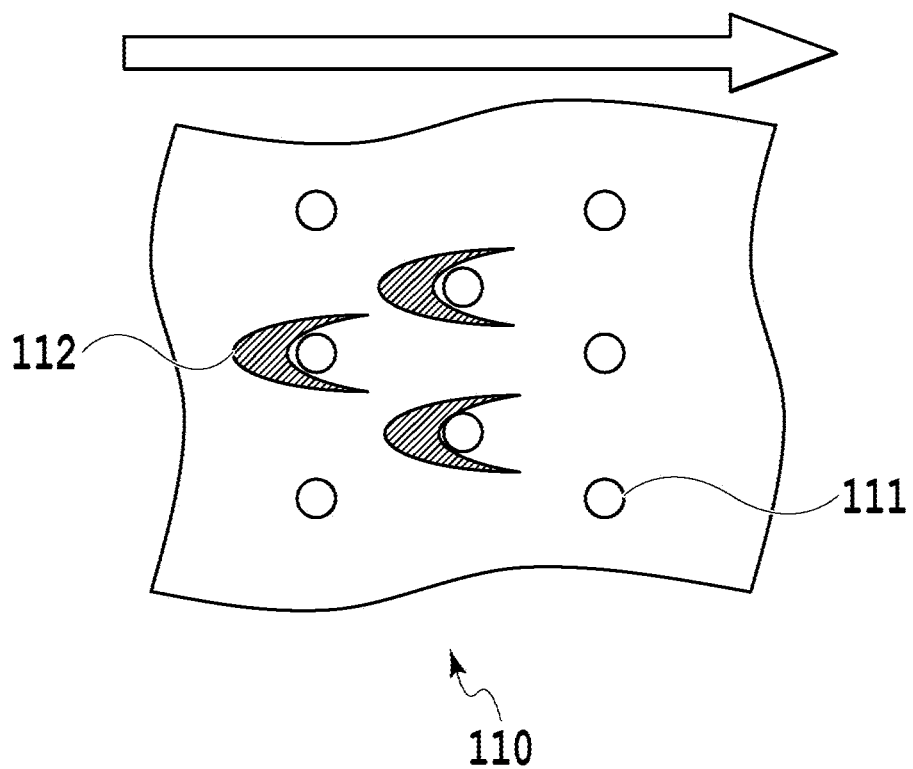
FIG. 10 is a schematic view explaining a method for removing minute aggregates related to the embodiment of the present invention.

3. Principle for Removal of Minute Aggregates Using Device of the Present Invention 3-1. Minute Aggregate-Removing Device of the Present Invention FIG. 10 is a schematic view explaining a basic structure 110 of the minute aggregate-removing structure to be used in the minute aggregate-removing method of the present invention. Structures 111 are arranged perpendicular to the flow direction of the fluid toward the arrow direction, and minute aggregates 112 in the sample are captured by the structures 111 along with the flow. A plurality of the structures 111 is provided at regular intervals parallel to the flow direction, and thus the minute aggregates are sequentially captured by the structures, and the minute aggregates in the sample are removed as the aggregates proceed downstream in the flow direction.

Figure 11:
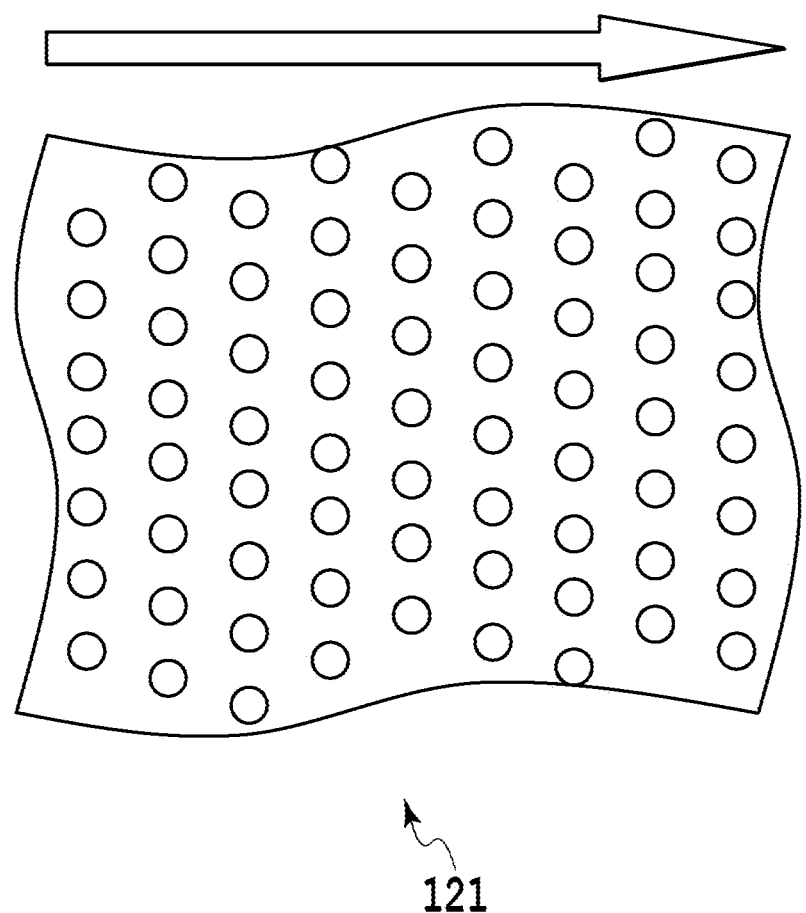
FIG. 11 is a schematic view explaining pillar structures of a minute aggregate-removing device related to the embodiment of the present invention.

FIG. 11 is an explanatory drawing showing a state where the minute aggregate-removing structure is constituted by pillar structures 121 at regular intervals. A flow which bypasses the minute aggregate-capturing portion is sequentially generated by arrangement of the pillar structures according to a fixed rule, and thereby the minute aggregates can be sequentially removed in an efficient manner. As described above, loss of the targeted cell or the like can be avoided and the cell can be treated without slowdown of the flow rate, by the bypass of the flow.

Although the shape of the pillar may be, for example, a columnar structure, the shape is not particularly limited as long as the pillar has a structure capable of capturing the targeted minute aggregates, and the pillar may also have, for example, a polygonal columnar structure in which the horizontal cross-sectional shape is rhombus. The diameter of each pillar may be, for example, approximately 5 to 30 µm.

Furthermore, in the pillar structures, the basic structures of its shape may be continuously arranged at regular intervals and can also be arranged with the gradually changing shape and arrangement depending on the purpose. In this way, the pillar structures are not limited to the case where they are arranged at regular intervals over the whole minute aggregate-removing structure and may be randomly arranged. For example, in the upstream in the flow direction, the structures may be arranged so that the arrangement interval is large and the arrangement interval becomes gradually narrow with the approach of the downstream. Furthermore, the pillar structures may be placed in only a part of the removal structure, and the pillar structures with different basic structures may be placed in a specific portion of the removal structure. In addition, the width of the entire channel may not necessarily be uniform, and the channel may have a shape in which the width of the channel is narrowed in the middle as necessary.

In a case where this arrangement interval of the pillars is excessively narrowed, the minute aggregates are sequentially captured from the upstream portion in the flow direction, and thus clogging is likely to be generated preferentially from the upstream portion. Accordingly, in a case where large size minute aggregates or a large amount of the minute aggregates are contained in the sample, it is preferable to take larger arrangement intervals of the pillars in the upstream portions in the flow direction, whereas, in the downstream portion in the flow direction, the arrangement intervals are gradually narrowed compared with in the upstream portion so as to capture smaller minute aggregates that were not able to be captured in the upstream portion in the flow direction. In a case where the arrangement intervals of the pillars in the upstream portion are narrow from the start area, clogging is generated in the removal structure due to the captured minute aggregates, and thus the treatment may become impossible, and loss may be generated due to captured targeted cells and the like.

In a case where the pillar structures are arranged linearly relative to the flow direction, the minute aggregates may reach the downstream as they are without being captured. Accordingly, from the viewpoint of the purpose of capturing and removing the minute aggregates of the present invention, it is preferable that the pillar structures are not arranged linearly relative to the flow direction. For example, preferably the pillars can be arranged with respect to the flow direction so that one row is deviated every time when approximately 5 to 30 pillars are arranged in the flow direction, and it is preferable that one raw is deviated every time when 10 to 20 pillars are arranged in the flow direction, for maintaining the thereby flow to efficiently separate the minute aggregates.

Preferably, the arrangement interval of the pillars is no smaller than the size of the targeted cell (including a complex of the targeted cell and the carrier substances) contained in the cell suspension. In a case where the arrangement interval is smaller than the size of the targeted cell, the targeted cell (the complex of the targeted cell and the carrier substance) is captured between the pillars, and thus the targeted cell is lost.

For example, since each size of cells contained in blood is generally at most approximately 30 µm, in a case where the purpose is to separate all cells in blood, the arrangement interval is preferably set to be not smaller than 30 µm. For example, in a case or the like where the purpose is to separate red blood cells and platelets and it is necessary to remove white blood cells, the arrangement interval can be set to be not smaller than 8 µm which is the size allowing these cells to be classified.

In addition, minute aggregates can also be removed after a complex is obtained by previously combining a carrier substance with a targeted cell in a cell suspension. In this case, the arrangement interval is preferably not smaller than the size of this complex since the targeted cell (complex of the targeted cell and the carrier substance) is lost due to being captured between the pillars. Specifically, the carrier substance can be exemplified by beads or the like labeled with an antibody or the like, but is not limited thereto, and an arbitrary substance may be considered as a carrier substance.

For example, in a case where there is formed a complex of a carrier substance having a size of 30 μm to be used and a cell having an approximate size of 20 μm, the arrangement interval of the pillars is preferably set to be not smaller than 50 μm.

Furthermore, the arrangement intervals of the pillars preferably include portions not larger than 200 μm. Since the minute aggregates also have relatively small sizes, the minute aggregates may not be completely removed in a case where all the pillar arrangement intervals in the removal structure are set to be not smaller than 200 μm. However, all the pillar arrangement intervals are not required to be not larger than 200 μm, and pillar structures having further larger arrangement intervals can be provided depending on the purpose.

As described above, in the minute aggregate-removing device of the present invention, the microchannel structure (in the present specification, referred to as "second microchannel structure" in some cases) which serves as a minute aggregate-removing structure, is preferably composed of pillars arranged at interval larger than 30 μm, and is also preferably composed of pillars arranged at interval not larger than 200 μm. The pillar arrangement interval of this microchannel structure depends on the sizes of the targeted cell (complex of the targeted cell and the carrier substance) and the minute aggregate to be removed, but in a case of removing minute aggregates from the blood, the pillar arrangement interval may be set to, for example, 50 μm to 200 μm, more preferably 70 μm to 170 μm, and further preferably 90 μm to 150 μm. Note that this pillar arrangement interval means an average interval in a case where pillars are arranged at two or more different intervals in the microchannel structure.

On the other hand, the complex in which the targeted cell is combined with the carrier substance is larger than the targeted cell by the size of the carrier substance. Accordingly, in a case where this complex is formed in blood, the pillar arrangement interval is preferably extended by only the size of the carrier substance, in order to remove the minute aggregates in blood and recover the complex (in order to prevent clogging). For example, in a case where a carrier substance having a diameter of 30 to 50 μm is used, the pillar arrangement interval may be set to, for example, 80 to 250 μm, more preferably 100 to 230 μm, and further preferably 120 to 220 μm.

As described above, a plurality of microchannel structure portions may be provided in the minute aggregate-removing device. Although the efficiency for removing the minute aggregates is enhanced by provision of a plurality of microchannel structure portions, it is preferable to provide two microchannel structure portions from the viewpoints of the recovery efficiency of the targeted cell (complex of the targeted cell and the carrier substance) and simplification of the device structure.

Figure 13:
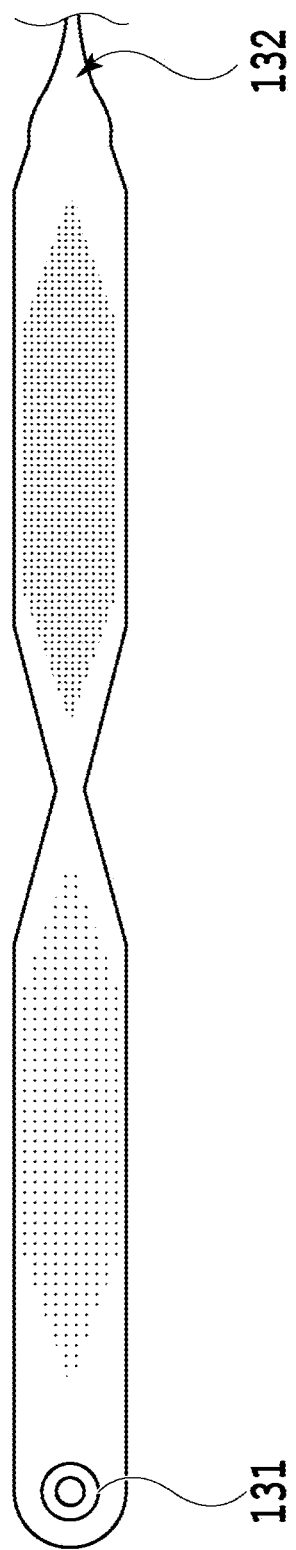
FIG. 13 is a schematic view explaining the minute aggregate-removing device (aspect having two microchannel structures) related to the embodiment of the present invention.
Figure 20A:
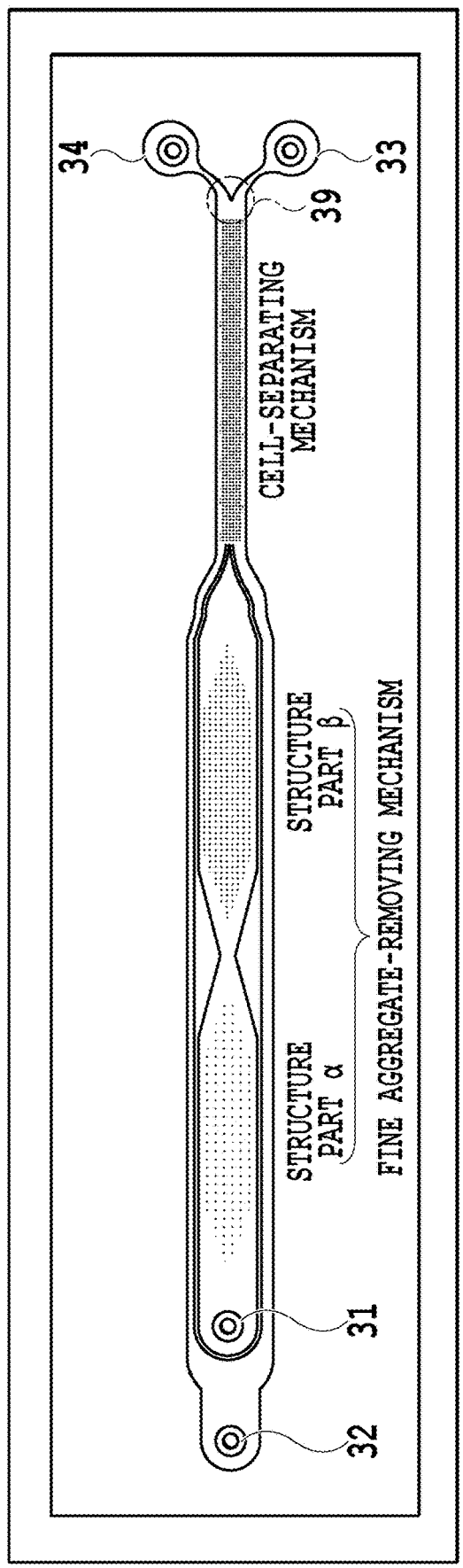
FIG. 20A is a plane view showing an example of an integrated cell-separating device.

In a case where two microchannel structure portions are provided, a portion for converging the width of the flow is preferably provided in the middle thereof (FIG. 13). This portion is narrower than the microchannel structure portion and has no pillar arranged. In this portion, the minute aggregates having passed through the first microchannel structure portion (structure portion α) are accumulated and flow to the next microchannel structure portion (structure portion β) (FIG. 13 and FIG. 20A). The minute aggregates can be efficiently removed by provision of such a portion that converges the width of the flow.

As described above, in a case where two or more microchannel structure portions are provided, in the minute aggregate-removing device, the pillar arrangement interval of the microchannel structure portion (structure portion β) on the downstream side from which the targeted cell is discharged may be set to 80 μm to 250 μm as described above, preferably 100 μm to 230 μm, and more preferably 120 μm to 220 μm. In addition, the pillar arrangement interval in the microchannel structure portion (structure portion α) on the upstream side into which the solution containing the targeted cell is introduced is set to be equal to or wider than that in the microchannel structure portion (structure portion β) on the downstream side, and thus it becomes possible to enhance the efficiency of removing the minute aggregates and to treat a relatively large number of samples while preventing clogging caused by the minute aggregates.

In addition, one aspect of the present invention is a minute aggregate-removing device which includes a removal structure having a microchannel structure as described above, wherein a sample inlet can be provided at the front of the microchannel and a sample outlet can be provided at the back of the microchannel.

Figure 12:
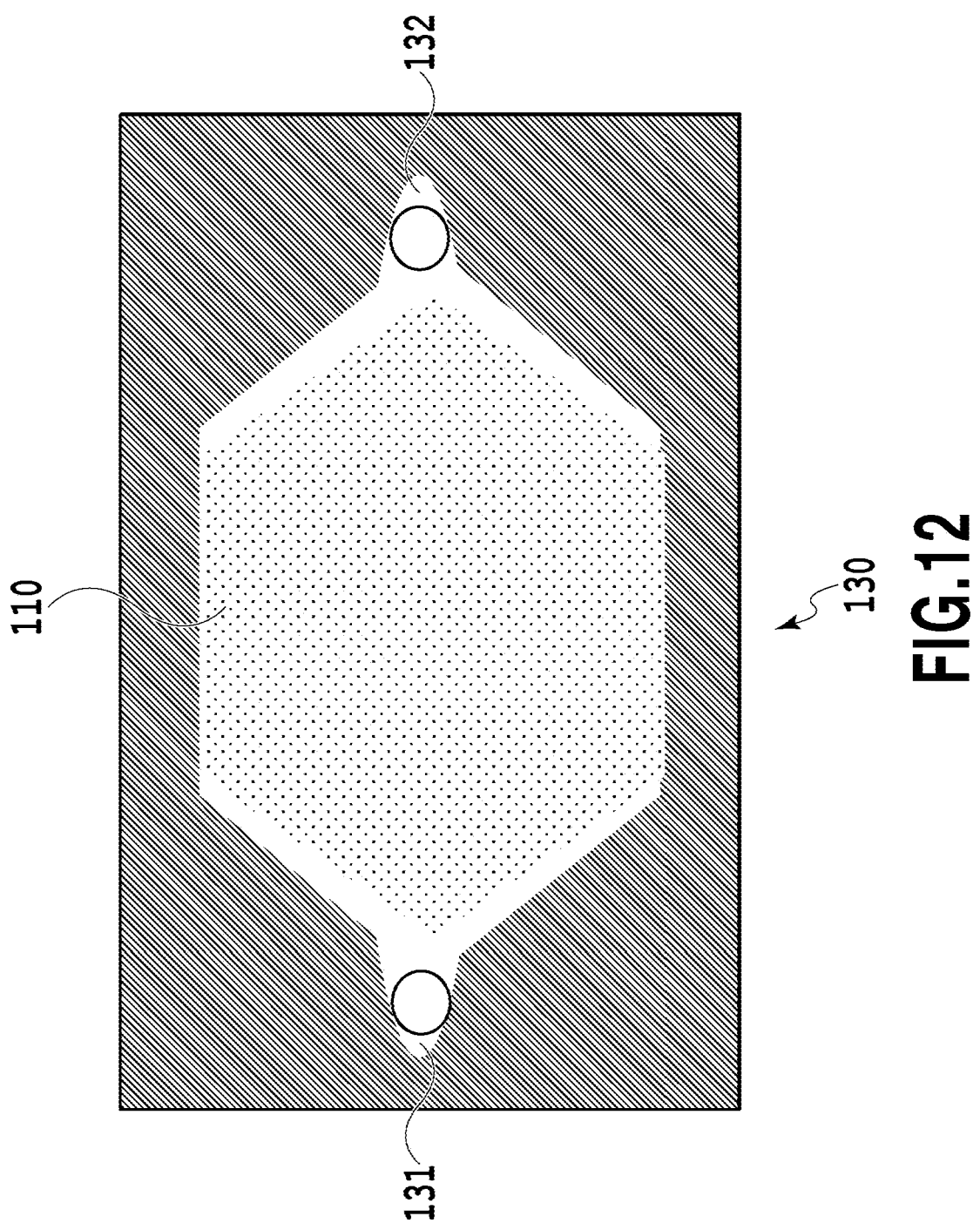
FIG. 12 is a schematic view explaining the minute aggregate-removing device related to the embodiment of the present invention.

3-2. Specific Example of Minute Aggregate-Removing Device of the Present Invention FIG. 12 is a schematic view explaining the minute aggregate-removing device as one embodiment of the present invention.

Hereinafter, a basic structure of a microchannel in a minute aggregate-removing device 130 will be explained with reference to the top view. First, the minute aggregate-removing device 130 includes a sample inlet 131 as a sample entrance structure and a sample outlet 132 as a fluid exit structure, and the basic structure 110 of the microchannel for removing the minute aggregates (minute aggregate-removing structure) is continuously provided between the sample inlet 131 and the sample outlet 132. As described above, this basic structure of the microchannel can provide, for example, two microchannel structure portions (FIG. 13).

Figure 14:
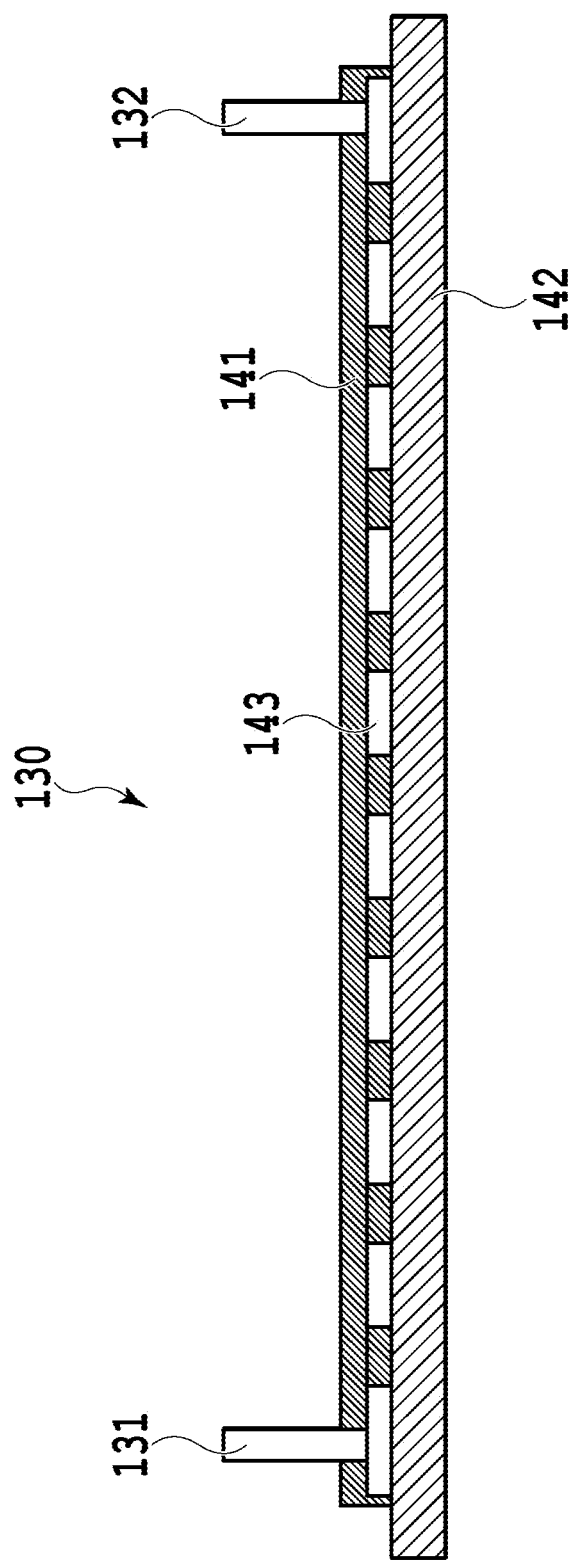
FIG. 14 is a cross-sectional schematic view of the minute aggregate-removing device in a side direction, related to the embodiment of the present invention.

FIG. 14 is a vertical cross-sectional schematic view of the minute aggregate-removing device related to the embodiment of the present invention. The minute aggregate-removing device 130 is composed of the basic structure 110 of the microchannel and is fabricated by joining, with a flat structure portion 142, a microchannel structure portion 141 including each shape of the inlet 131, the outlet 132 and the like, and has a channel space 143 in the space thereof. Furthermore, the basic structure 110 can also be used while changes are appropriately made at each portion of the inlet 131 and outlet 132, by proper joining of fluid feed tubes therewith and by provision of a joining portion with a syringe or the like. Moreover, although the inlet 131 and the outlet 132 are not particularly limited as long as they have structures allowing introduction of samples and recovery of an effluent, they may also include a structure or the like allowing fractionation immediately before or after treatment.

The channel structure (e.g. arrangement of the pillars) of the microchannel structure portion 141 can be fabricated by appropriate selection of a known method. There can be used, as a material for the member of the channel structure portion, for example, glass, silicone, dimethylpolysiloxane, plastic or the like. In addition, although the flat structure portion 142 is not particularly limited as long as its material is flat and can be joined with the channel structure portion 141, but a strong glass, strong plastic or the like is preferably used. Furthermore, a transparent member is preferable, since the inside of the channel can be easily observed and there can be grasped whether or not the minute aggregates are removed and the targeted cell is lost.

Note that the minute aggregate-removing device 130 of the present invention includes each shape of the basic structure 110, the inlet 131, the outlet 132 and the like in the microchannel, and can also have a structure including the channel space 143 of the microchannel, for example, a structure including each shape of the basic structures 110, the inlet 131, the outlet 132 and the like on the member of the flat structure portion 142 side shown in the figure.

Although the minute aggregate-removing device 130 of the present invention can be used alone, it can be used as a serial system by connection to an arbitrary cell-separating device by the use of a fluid feed tube or the like included at the outlet 132, and a method for using it can be selected depending on the purpose.

3-3. Integrated Cell-Separating Device

Figure 15:
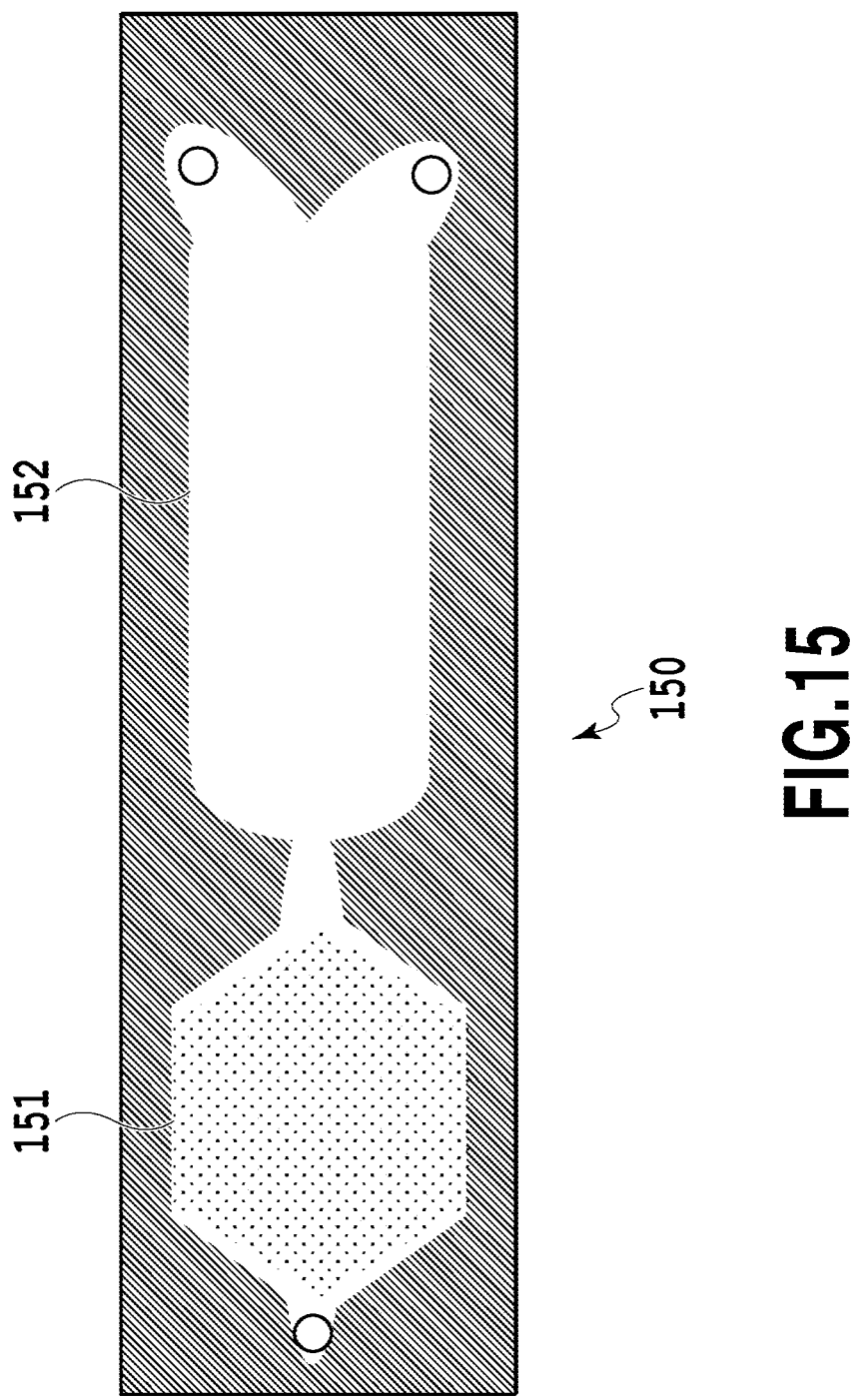
FIG. 15 is a schematic view explaining the cell-separating device including the minute aggregate-removing structure related to the embodiment of the present invention.

FIG. 15 is a schematic view explaining an integrated minute cell-separating device 150 showing another embodiment of the present invention. As described above, the minute aggregate-removing device of the present invention can be used as a serial system by being connected to the cell-separating device. In this case, the device is preferably used as a cell-separating device integrally including a minute aggregate-removing device and a cell-separating device, from the viewpoints of convenience for use and manufacturing cost. In addition, the device can also be an integrated device in such a way, as necessary, since loss of the sample in the tube used for connection can also be reduced.

In addition, this cell-separating device is preferably a separation structure for fractionation depending on the size of the cell to be separated (size fractionation). Since the influence on the fractionation can be eliminated by removal of the minute aggregates in the sample, the effect of the separation structure can be exhibited to the maximum and the separation accuracy can be enhanced. The separation structure based on size fractionation can be exemplified by a cell-separating device based on the DLD principle. The cell-separating device based on the DLD principle can be manufactured by the aforementioned method. Additionally, among the integrated cell-separating devices, an integrated cell-separating device in which the cell-separating device based on the DLD principle is joined to a back of the minute aggregate-removing device including two separate microchannel structure portions as described above is preferable (FIG. 20A and FIG. 20B). In the integrated cell-separating device as shown in FIG. 20A, the buffer solution is introduced from the buffer inlet 32, flows outside the minute aggregate-removing structure (structure portions α and β), joins the cell suspension from which the minute aggregates have been removed, and flows into the cell-separating structure (cell-separating portion). Namely, in the configuration of FIG. 20A, the buffer solution introduced from the buffer inlet 32 is not introduced into the minute aggregate-removing structure.

4. Method for Removing Minute Aggregates of the Present Invention

The method for removing the minute aggregates of the present invention is a method for removing the minute aggregates from a cell suspension (sample) such as blood in a continuous fluid flow as described above. Note that the cell suspension (sample) is not particularly limited, but can be exemplified by body fluids such as blood, lymph, saliva, urine and tear. These may be used as they are, and may be diluted with an arbitrary buffer solution. In addition, the buffer solution to be used can be appropriately selected and used depending on the targeted cell suspension (sample), the targeted cell to be separated and the contained minute aggregates. There can be used, as the buffer solution, one of or a combination of plural isotonic solutions in order to avoid influence on the cells, and there may be used, for example, saline, PBS, or the like.

Although the minute aggregates to be removed in the present invention are also contained in a suspension of cultured cells or the like, the method for removing the minute aggregates of the present invention is suitable as a cell suspension (sample), particularly in a case of using blood. The minute aggregates in the blood are derived from ones obtained by aggregating fibrin, other denatured proteins, fats and the like, and since they are particularly viscous, they are easily captured by the pillar structures in the removal structure, and are suitable as target samples in the method of the present invention because the minute aggregates are rarely released and flow out to the downstream in the flow direction after they are once captured by the pillar structures.

A first aspect of the present invention is a method for removing minute aggregates from a cell suspension containing a targeted cell and minute aggregates in a continuous fluid flow, which includes steps of allowing a cell suspension or a liquid mixture of the cell suspension and a buffer solution to flow into a minute aggregate-removing device including a microchannel structure (minute aggregate-removing structure) and to pass through the microchannel in the minute aggregate-removing device to capture the minute aggregate. Note that a step of recovering the targeted cell may be provided after the step of capturing the minute aggregates.

In the present invention, the cell suspension and the buffer solution are added to the minute aggregate-removing device of the present invention. In this case, the buffer solution may be previously allowed to flow and then the cell suspension may be added, or the cell suspension may be added after being diluted by mixing with the buffer solution. Additionally, in the removal method of the present invention, the minute aggregates in the cell suspension are captured and removed by the step of capturing the minute aggregates, and the cell suspension containing the targeted cell is recovered from the outlet of the removal device, as described above. Additionally, in a case of providing a fluid feed tube or the like on the outlet of the removal device, the suspension is recovered through the tube or the like. Furthermore, in a case of adopting a serial system by connecting with the cell-separating device (including an integrated cell-separating device) as described above, the cell suspension recovered after removing the minute aggregates is then subjected to cell separation. Note that the ratio of the cell suspension to the buffer solution is not particularly limited, and the flow rate of the cell suspension is not particularly limited either. In relation to this flow rate, the rate can be appropriately adjusted by installation of a pump or the like on either the inlet or the outlet or both of the inlet and the outlet of the minute aggregate-removing device of the present invention.

The method of the present invention is a method used for pretreatment in accurately fractionating the contained targeted cell from a cell suspension containing cells such as blood, and in the subsequent cell separation step, the targeted cell can be more accurately fractionated by removal, without loss, of the targeted cell in the sample and by removal, with high precision, of the minute aggregates in the sample.

In another aspect of the present invention, the method for removing minute aggregates from blood of the present invention includes an aspect of adding a blood anticoagulant reagent. The minute aggregates are already present in blood, and furthermore new minute aggregates may be generated in the process of treating the blood. Accordingly, although the already existing minute aggregates can be removed by the aforementioned method of the present invention, the blood anticoagulant reagent is preferably added to the composition of its dilution buffer in order to prevent the new minute aggregates from being generated during treatment of blood. Then, by addition of the blood anti coagulant reagent, the blood from which the minute aggregates have been removed can be suitably used for the subsequent blood test and various treatments (including separation of blood components, etc.) by the use of the method for removing the minute aggregates of the present invention.

The blood anticoagulant reagent is exemplified by sodium citrate, EDTA, heparin, or the like, and a thrombin inhibitor is preferably used among them, and a reagent such as PPACK is more preferably used.

Although sodium citrate, EDTA, and the like inhibit calcium ions and indirectly inhibit a blood coagulating action, it is more effective to directly inhibit thrombin as a coagulation factor. In addition, heparin inhibits only free thrombin as a thrombin inhibitor, but PPACK ($C_{21}H_{31}ClN_6O_3 \cdot 2HCl$) [1-(2-Amino-3-phenylpropanoyl)-N-[1-chloro-6-(diaminomethyl ideneamino)-2-oxohexan-3-yl]pyrrolidine-2-carboxamide] is more effective because it acts on both free thrombin and bound thrombin.

The removal method of the present invention is for removing minute aggregates already present in blood and characterized in that the minute aggregates already present in the blood can be removed while suppression of new production of minute aggregates in blood, by combining a thrombin inhibitor such as PPACK.

In the present invention, the minute aggregate-removing device having the aforementioned microchannel structures is combined with the dilution buffer solution containing the thrombin inhibitor, and thus clogging of the minute aggregates can be suitably eliminated during use of the minute aggregate-removing device of the present invention and a cell-separating device arbitrarily and selectively connected. As a result, the removal method using the minute aggregate-removing device of the present invention allows efficient and successive removal of the minute aggregates and separation of cellular components.

Although, hereinbefore, the embodiments of the present invention have been described in detail, the present invention is not actually limited to the aforementioned embodiments and any changes within the scope not departing from the gist of the present invention are included in the present invention.

EXAMPLES

Hereinafter, the present embodiments will be explained in detail by giving Examples. However, the present embodiments are not actually limited to the following Examples.

1. Example of Cell Separation (1) Cell-Separating Device Used in Examples

This example is intended to separate a tumor cell in blood. For this purpose, 30 μm beads carrying antibodies were used as target-capturing molecules. Then, on the basis of a principle of Deterministic Lateral Displacement, dimethylpolysiloxane (PDMS) was used to fabricate a cell-separating device including a basic structure (separation area) having a DLD microchannel structure with a particle size of 40 μm set as a separation threshold Dc.

Specifically, the cell-separating device has a basic structure, in which $$G \approx 2.62057 Dc \qquad \text{Formula 3}$$

pillars having a diameter of 15 μm are arranged at intervals of 104.8 μm, from G=104.8 μm obtained by substitution of Dc=40 μm in the above Formula 3, and the pillars are arranged so that one row is deviated every 15 columns, from $\varepsilon = \tan \theta = 1/15$ as a suitable condition for the separation (see FIG. 1). In addition, a height of the channel space was set to 50 μm.

More specifically, a mask was used to fabricate a resist mold so as to have the aforementioned basic structure, then a dimethylpolysiloxane (PDMS) is molded to fabricate a PDMS channel in which pillars are arranged at uniform intervals, thereby forming the basic structure portion 36 of the DLD microchannel having micropillar structures. In addition, on one side of the both ends of the basic structure portion 36, port holes are formed, where the sample inlet 31 and the buffer inlet 32 are provided, and on the other side, the first outlet 33 and the second outlet 34 are provided. Then, the basic structure portion was joined with the glass substrate 37 and thus the channel space 35 was formed in the space between the basic structure portion and the substrate. In addition, tubes were attached to the sample inlet 31 and the buffer inlet 32 as well as the first outlet 33 and the second outlet 34, and thus the cell-separating device was fabricated. This cell-separating device was used in Examples 1 to 3.

In Example 4, the cell-separating device having a similar configuration was fabricated and used, except that basic structures of a structure portion a (60a) having a particle size of 10 μm set as a separation threshold and of a structure portion b (60b) having a particle size of 40 μm set as a separation threshold are provided.

(2) Evaluation of Whether or not Cell was Separated

The cell separation was performed on a microscope stage in Examples, and it was visually confirmed whether or not the cell was separated. Specifically, PBS was allowed to flow from the buffer channel port at 100 μl/min, and a cell suspension was allowed to flow from a sample inlet at 100 μl/min for 10 minutes. After selection, the recovered sample was observed with a transmission optical microscope and a fluorescence microscope.

Example 1

Figure 8:
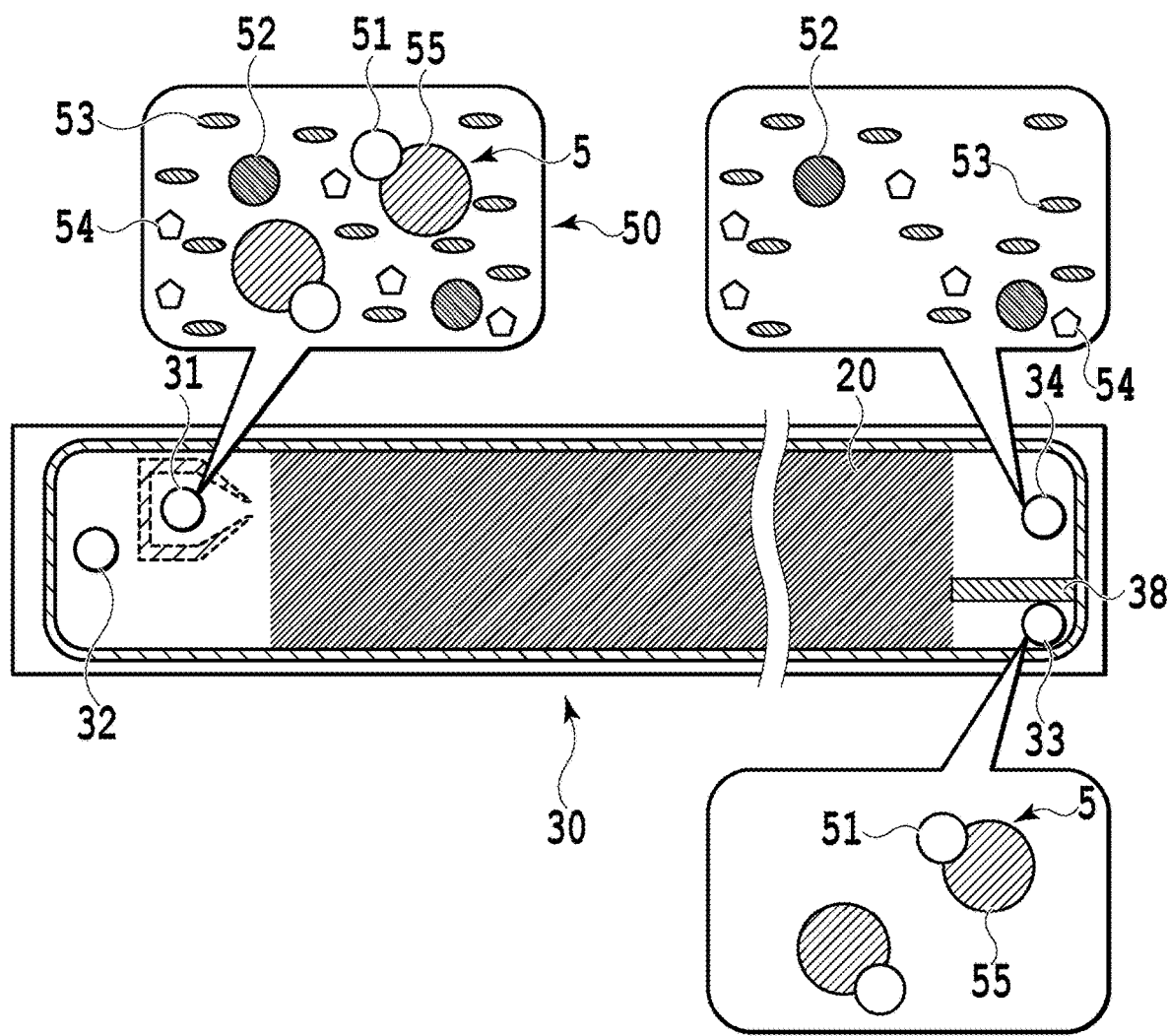
FIG. 8 is a schematic view for explaining Examples 1 to 3 of the present invention.

FIG. 8 is a view for explaining the Example. The example was performed for the purpose of separating a human breast cancer-derived cell (MCF-7) contaminated in whole blood. First, a sample was prepared by addition of a human breast cancer-derived cell (DS Pharma Biomedical Co., Ltd.) 51 to normal whole blood diluted with a PBS buffer. There was added, to this sample, anti-EpCAM antibody-labeled beads (CD326 (EpCAM), Human, pluriBeads, s-beads: pluriSelect Life Science UG & Co.KG) 55 having a particle size of 30 μm carrying a monoclonal antibody against human EpCAM (anti-EpCAM antibody) as a target-capturing molecule, and the incubation while stirring the resulting substance at room temperature gave a sample 50. The cell-separating device 30 having a particle size of 40 μm set as a separation threshold was previously filled with PBS, and the sample 50 after the reaction was fed to the sample inlet 31 at a rate of 100 μl/min by the use of a syringe pump. Furthermore, at the same time, PBS was fed to the buffer inlet 32 at a rate of 100 μl/min. With respect to the microscopic observation of the recovered sample, the observation of morphology was carried out with a transmission optical microscope, and in addition, staining with a nucleated cell staining reagent (Hoechst 33342 solution: Takara Bio Inc.) for staining cancer cells and white blood cells, staining with an anti-cytokeratin antibody (Anti-pan Cytokeratin antibody [PCK-26] (FITC): Abcam plc.) for staining cancer cells, and staining with an anti-CD45 antibody (Anti-CD45-APC, Mono (ML2): Funakoshi Co., Ltd.) for staining white blood cells were carried out in order to distinguish cells depending on their properties, and then observation and confirmation with a fluorescence microscope were carried out.

As a result, it was confirmed that, among the components in the whole blood, white blood cells 52, red blood cells 53, platelets 54, and the like had been recovered from the second outlet 34. Furthermore, the human breast cancer-derived cell 51 having formed the complex 5 together with the anti-EpCAM antibody-labeled beads 55 was selectively discharged from the first outlet 33. As described above in the Example, it was confirmed with the microscope that the human breast cancer-derived cell 51 having formed the complex 5 together with the anti-EpCAM antibody-labeled beads 55 was able to be selectively separated (FIG. 8).

Example 2

As with Example 1, a similar procedure was carried out by the use of a sample obtained by addition of a human prostate cancer-derived cell (LNCap) (DS Pharma Biomedical Co., Ltd.) to normal whole blood instead of the human breast cancer-derived cell (MCF-7), and as a result, it was confirmed that, among the components in the whole blood, white blood cells, red blood cells, platelets, and the like was recovered from the second outlet. In addition, the human prostate cancer-derived cell having formed the complex together with the anti-EpCAM antibody-labeled beads was selectively discharged from the first outlet. As described above in the Example, it was confirmed with a microscope that the human prostate cancer-derived cell which had formed the complex 5 together with the anti-EpCAM antibody-labeled beads 55 was able to be selectively separated.

Example 3

As with Examples 1 and 2, a similar procedure was carried out by the use of a cancer-carrying patient-derived blood instead of the sample obtained by addition of the human-derived cancer cell to the normal whole blood, and as a result, it was confirmed that an epithelial tumor cell expressing the EpCAM was able to be accurately separated.

Comparative Example 1

In a case where separation of the diluted cancer-carrying patient-derived blood was attempted by the cell-separating device without using the anti-EpCAM antibody-labeled beads as a comparative example, white blood cells and epithelial tumor cells whose sizes partially overlap with each other were not able to be separated.

Example 4

Figure 9:
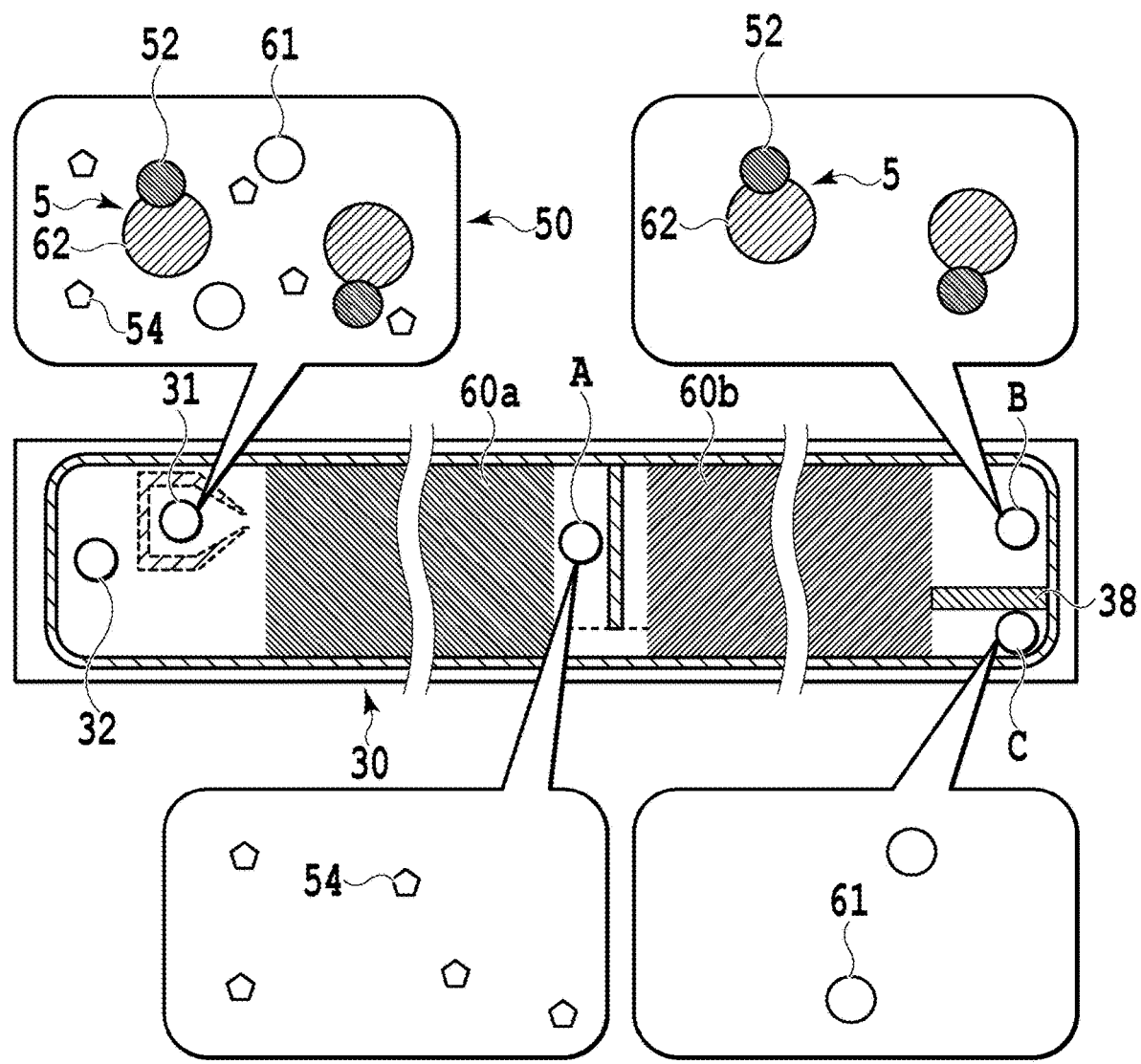
FIG. 9 is a schematic view for explaining Example 4 of the present invention.

It is known that there is a group of cells with weak expression of EpCAM among epithelial tumor cells in blood of cancer-carrying patients. Therefore, there were concerns about missing of a targeted epithelial tumor cell in the method using the anti-EpCAM antibody-labeled beads. Accordingly, the separation of an epithelial tumor cell in blood of a cancer-carrying patient was attempted with higher accuracy. FIG. 9 is a view for explaining the Example.

First, hemolytic treatment was carried out by ammonium chloride treatment, anti-CD45 antibody-labeled beads (pluriSelect Life Science UG: CD45, Human, pluriBeads, s-beads) 62 with a particle size of 30 µm carrying a monoclonal antibody against human CD45 (anti-CD45 antibody) as a target-capturing molecule were added to a cancer-carrying patient blood from which red blood cells had been removed, and incubated while stirring at room temperature to thereby give the sample 50. The cell-separating device 30 having structures of the structure portion a (60a) with a particle size of 10 µm set as a separation threshold and of the structure portion b (60b) with a particle size of 40 µm set as a separation threshold was previously filled with PBS, and the sample after the reaction was fed to the sample inlet 31 at a rate of 100 µl/min by the use of a syringe pump. Furthermore, at the same time, PBS was fed to the buffer inlet 32 at a rate of 100 µl/min.

As a result, it was confirmed that, among the components in the whole blood, the platelet 54 and the cell residue having a size smaller than 10 µm were first recovered from the outlet A (A) by the structure portion a (60a). Moreover, it was confirmed that the complex 5 of the leucocyte 52 and the anti-CD45 antibody-labeled beads 62 having a particle size larger than 40 µm was recovered from the outlet B (B) by the structure portion b (60b). Furthermore, it was confirmed with a microscope that an epithelial tumor cell 61 having a particle size smaller than 40 µm was recovered from the outlet C (C).

2. Example for Removal of Minute Aggregates

The Example is aimed at removal of minute aggregates in a sample by the use of a normal human whole blood [manufactured by Kohjin Bio Co., Ltd.] as a sample.

Example 5

Figure 16:
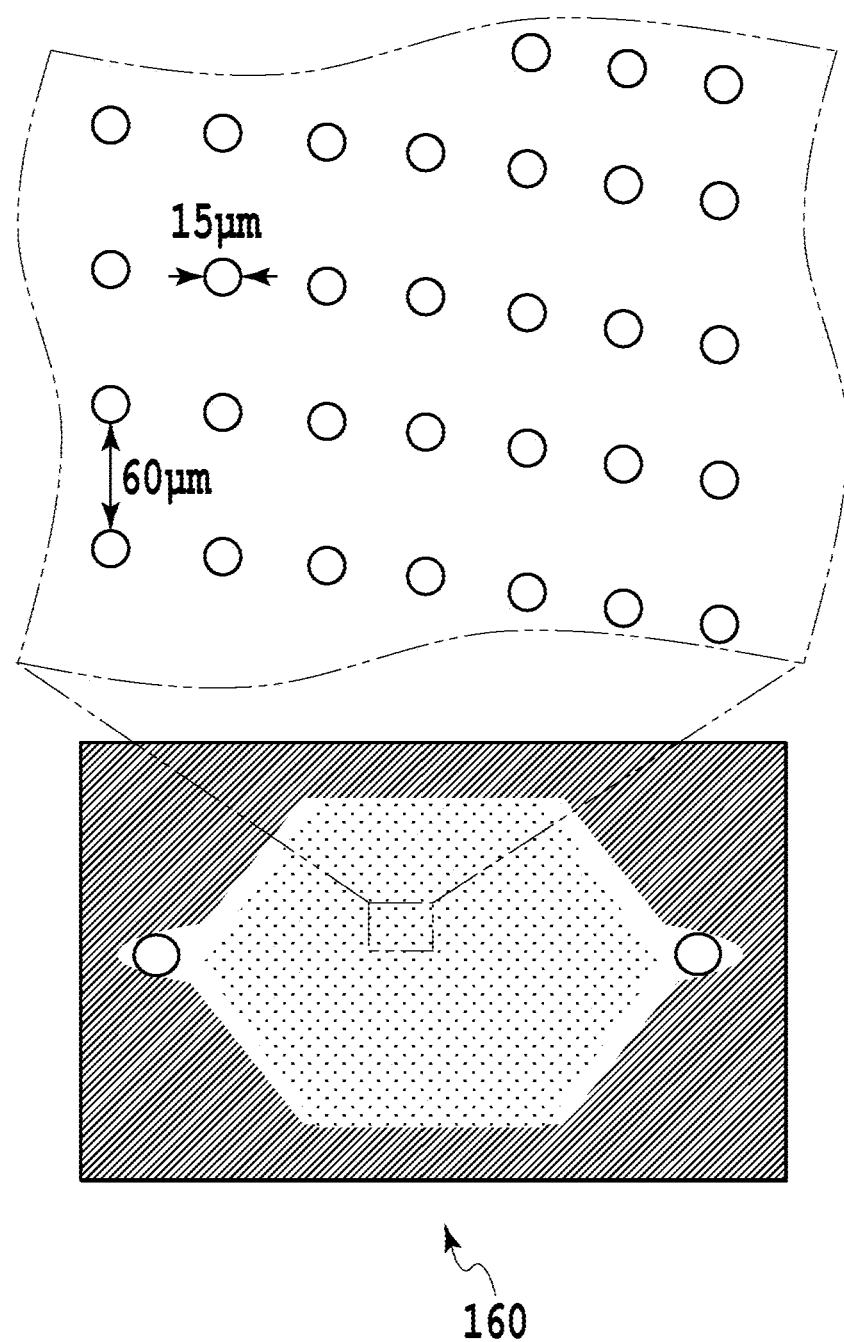
FIG. 16 is a schematic view for explaining Examples of the present invention.

FIG. 16 is a schematic view for explaining Examples of the present invention. Hereinafter, the structure of the removal structure having the microchannel structure in the minute aggregate-removing device 160 used in Examples will be explained with reference to the top view. The minute aggregate-removing structure in the minute aggregate-removing device has pillar structures [Pillar diameter: 15 µm, Pillar interval: 60 µm, the pillars are arranged so that one row is deviated every 15 columns relative to the flow direction, Channel depth: 50 µm] shown in FIG. 16.

More specifically, a mask was used to fabricate a resist mold so as to have the aforementioned microchannel structure, then a dimethylpolysiloxane (PDMS) is molded to fabricate a PDMS channel in which pillars are arranged at uniform intervals, thereby forming the basic structure portion 141 having the pillar structures shown in the schematic view of FIG. 14. In addition, port holes are formed on this basic structure portion 141, where the inlet 131 and the outlet 132 are provided. Then, the basic structure portion was joined with the flat structure portion 142 made of a glass substrate so that the channel space 143 was formed in the space between the basic structure portion and the substrate. Then, tubes were attached to the inlet 131 and the outlet 132, and thus the cell-separating device was fabricated. This minute aggregate-removing device was used in Examples.

A state of the removal of the minute aggregates was observed on the inverted microscope stage in visual and image observations, and was photographed as a video image. Specifically, a PBS buffer containing 0.05% Tween was previously allowed to pass through the inlet of the aforementioned minute aggregate-removing device to thereby remove air bubble from the channel, and then 1 mL of the aforementioned blood having been diluted by twice with a PBS buffer containing 0.05% Tween was treated by a syringe pump at a constant rate of 20 µL/min.

Figure 17A:
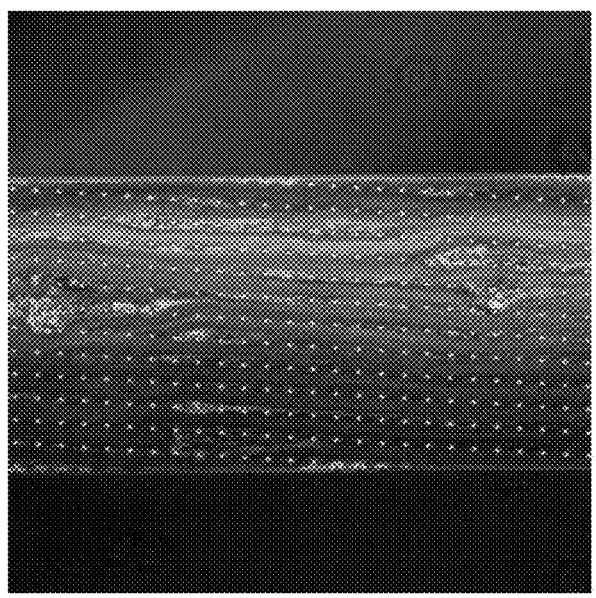
FIG. 17A is a view showing a state where the minute aggregates are removed (vicinity of the device inlet) for explaining Examples of the present invention.
Figure 17B:
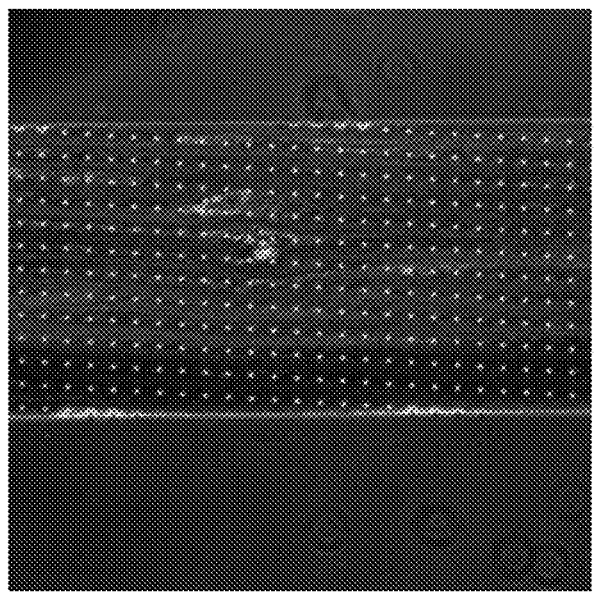
FIG. 17B is a view showing a state where the minute aggregates are removed (middle of the device) for explaining Examples of the present invention.
Figure 17C:
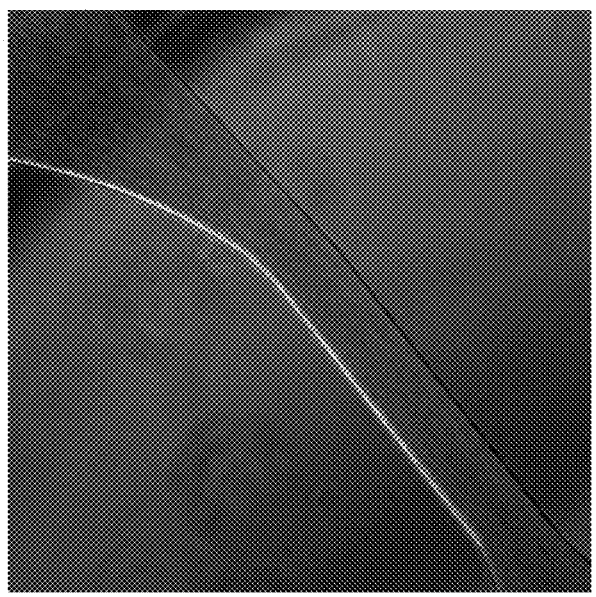
FIG. 17C is a view showing a state where the minute aggregates are removed (vicinity of the device outlet) for explaining Examples of the present invention.
Figure 17D:
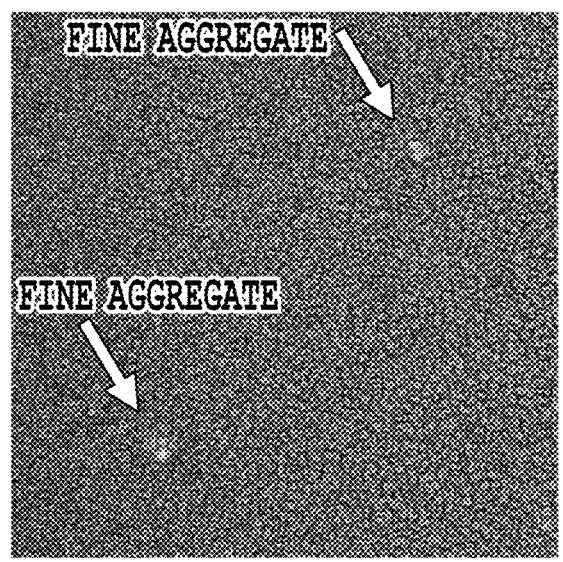
FIG. 17D is a view showing a state where the minute aggregates are removed (sample before treatment) for explaining Examples of the present invention.
Figure 17E:
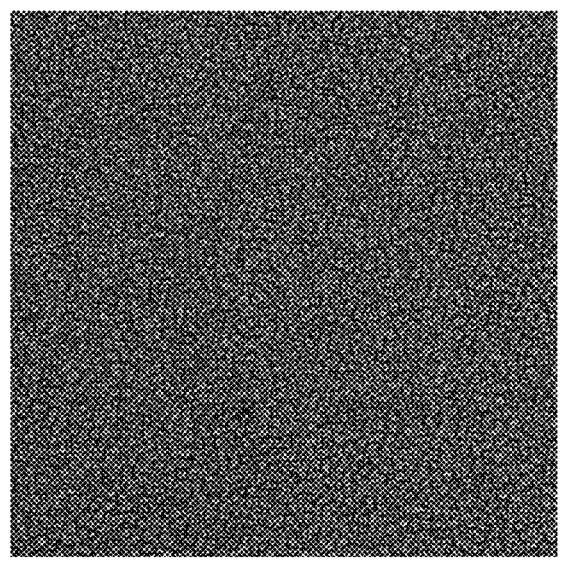
FIG. 17E is a view showing a state where the minute aggregates are removed (sample after treatment) for explaining Examples of the present invention.

As a result, as shown in FIG. 17A to FIG. 17E, a state where the minute aggregates were captured in the minute aggregate-removing device was observed. It was confirmed that a large number of minute aggregates were captured in the vicinity of the inlet (FIG. 17A), and the minute aggregates decreased with the approach of the outlet (FIG. 17B), and the minute aggregates disappeared in the vicinity of the outlet (FIG. 17C). In addition, the samples before and after passing through this minute aggregate-removing device were compared with each other and observed under the inverted microscope. It was confirmed that there were the minute aggregates before the sample passed through the device (FIG. 17D), but the minute aggregates were removed after the sample passed through the device and was treated (FIG. 17E).

Comparative Example 2

The sample was similarly treated in the same way as the method described in aforementioned Example 5 by the use of the minute aggregate-removing device fabricated except that only the pillar intervals were 10 μm. As a result, it was observed that, besides the minute aggregates, large cells such as white blood cells were accumulated between the pillars. In addition, clogging was generated in the device before 1 mL of the sample was completely treated, and the total volume was not able to be treated.

Examples 6 to 10 and Comparative Example 3

In the same way as Example 5, minute aggregate-removing devices each of which has a pillar interval (Gap) of 50 μm, 60 μm, 100 μm, 150 μm and 200 μm were fabricated (Examples 2 to 6, respectively). Additionally, as Comparative Example 2, a device in which the pillar interval was 60 μm and the pillars were arranged in a straight line was fabricated. Then, beads having a diameter of 30 μm mimicking the cell larger than that in the blood sample prepared as described above were added to the sample and allowed to pass through each device in the same way as Example 1, and the results are shown in Table 1. Respectively, a sample in which the minute aggregates (foreign substances) were able to be removed is marked with a double circle ⊙ a sample with substantial removal is marked with a circle ○, a sample with partial removal is marked with a triangle Δ, and furthermore, a sample with lost beads (clogging) is marked with a cross x, and a sample without loss (clogging) is marked with a circle ○.

TABLE 1

|  | Ex 6 | Ex 7 | Ex 8 | Ex 9 | Ex 10 | Comp Ex 3 |
| --- | --- | --- | --- | --- | --- | --- |
| Gap (μm) | 50 | 60 | 100 | 150 | 200 | 60(Linear arrangement) |
| Removal of foreign substances | ⊙ | ⊙ | ⊙ | ○ | Δ | Δ |
| Clogging of beads | X | X | ○ | ○ | ○ | X |

Example 11

The blood sample was treated by the use of a minute aggregate-removing device having a structure in which the minute aggregate-removing devices used in Example 10 (Gap width: 200 μm), Example 8 (Gap width: 100 μm), Example 7 (Gap width: 60 μm) are connected in series in this order, and as a result, the minute aggregates were able to be removed without loss of the beads from no less than 1 mL of blood sample.

Example 12

First, the outlet of the minute aggregate-removing device used in Example 11 is connected with the sample inlet of the separation device based on the DLD as a separation principle with a separation threshold of 30 μm, to thereby form an integrated cell-separating device. This integrated cell-separating device was previously filled with a PBS buffer containing 1% of BSA and 5 mM of EDTA. Next, a sample obtained by adding beads with a diameter of 30 μm mimicking cells to this integrated cell-separating device, by the use of a resulting solution obtained by diluting blood twice with PBS containing 1% of BSA and 5 mM of EDTA as a blood dilution buffer and by adding PPACK at a final concentration of 80 μM, was allowed to flow from the inlet of the minute aggregate-removing device. In addition, the buffer (PBS containing 1% of BSA and 5 mM of EDTA) was allowed to flow from the buffer inlet of the separation device. As a result, as shown in FIG. 18A, the 30 μm beads were able to be separated with no clogging in the separation device as shown in a portion surrounded by a dashed line in FIG. 18B.

Note that the separation device based on the DLD as a separation principle with a separation threshold of 30 μm was fabricated as follows. On the basis of the aforementioned principle of the Deterministic Lateral Displacement (DLD), dimethylpolysiloxane (PDMS) was used to fabricate a cell-separating device including a basic structure (separation structure) having a DLD microchannel structure with a particle size of 30 μm set as a separation threshold Dc.

Specifically, this cell-separating device has a basic structure, in which $$G \approx 2.62057 Dc \qquad \text{Formula 3}$$

from G=78.6 μm determined by substituting Dc=30 μm in the above Formula 3, pillars with a diameter of 15 μm are arranged at intervals of 78.6 μm, and from ε=tan θ=1/15 as a suitable condition for the separation, the pillars are arranged so that one row is deviated every 15 columns. In addition, a height of the channel space was set to 50 μm.

Specifically, a mask was used to fabricate a resist mold so as to have the basic structure, then a dimethylpolysiloxane (PDMS) was molded to fabricate a PDMS channel in which pillars were arranged at uniform intervals, thereby forming the basic structure portion of the DLD microchannel having micropillar structures.

Comparative Example 4

Figure 19:
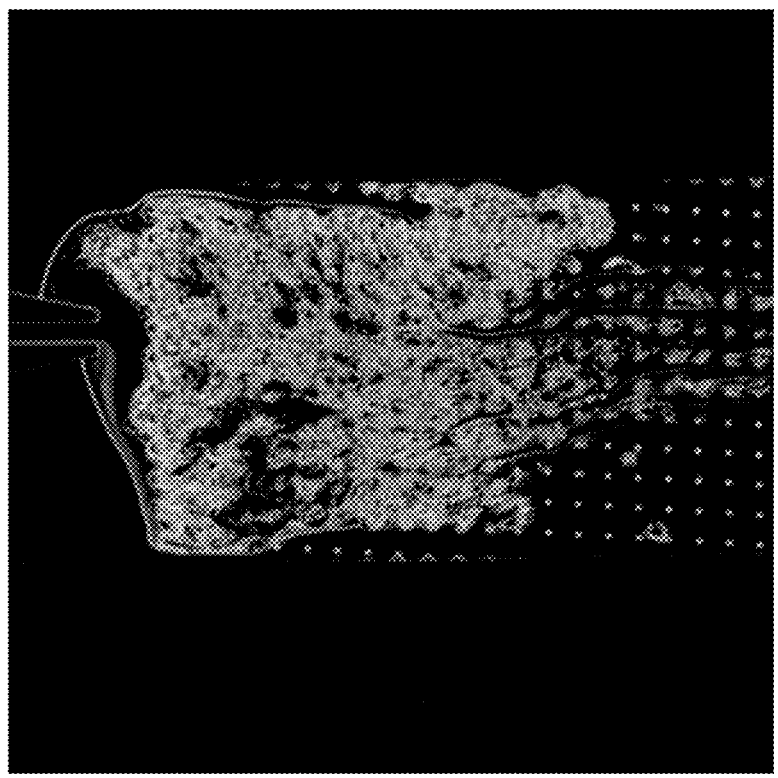
FIG. 19 is a view showing a state of clogging in the separation device for explaining Comparative Examples of the present invention.

In a case where a resulting solution obtained by diluting blood twice with PBS containing 1% of BSA and 5 mM of EDTA as a blood dilution buffer was allowed to pass directly through the separation device without allowing to pass through the minute aggregate-removing device, clogging was generated in the upstream of the separation device as shown in FIG. 19, and separation was not able to be performed.

Figure 20B:
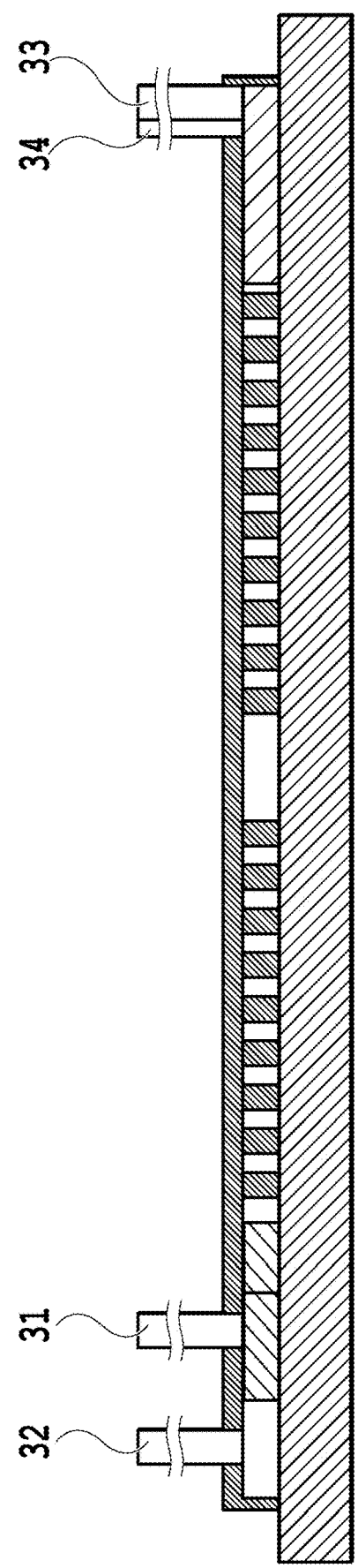
FIG. 20B is a side view showing an example of the integrated cell-separating device.

3. Example of Integrated Separation Device (1) Fabrication of Integrated Separation Device First, in the similar way to the aforementioned Example 5, there was designed a minute aggregate-removing device in which two microchannel structure portions (Structure portion α: pillar intervals are 200 μm, Structure portion β: pillar intervals are 150 μm) are connected in series (FIG. 13). Note that, in order to prevent clogging at the end of the channel, the outer lateral sides of the structure portion α and the structure portion β are not provided with a pillar within the area of 80 μm from the wall surface of the channel. In addition, a portion that converges the width of the flow is provided between the structure portion α and the structure portion β. An integrated cell-separating device was fabricated as a design in which the minute aggregate-removing device having these two structure portions was integrated with the separation device based on the DLD as a separation principle with a separation threshold of 30 μm (FIG. 20A and FIG. 20B).

(2) Preparation of Sample

Figure 22:
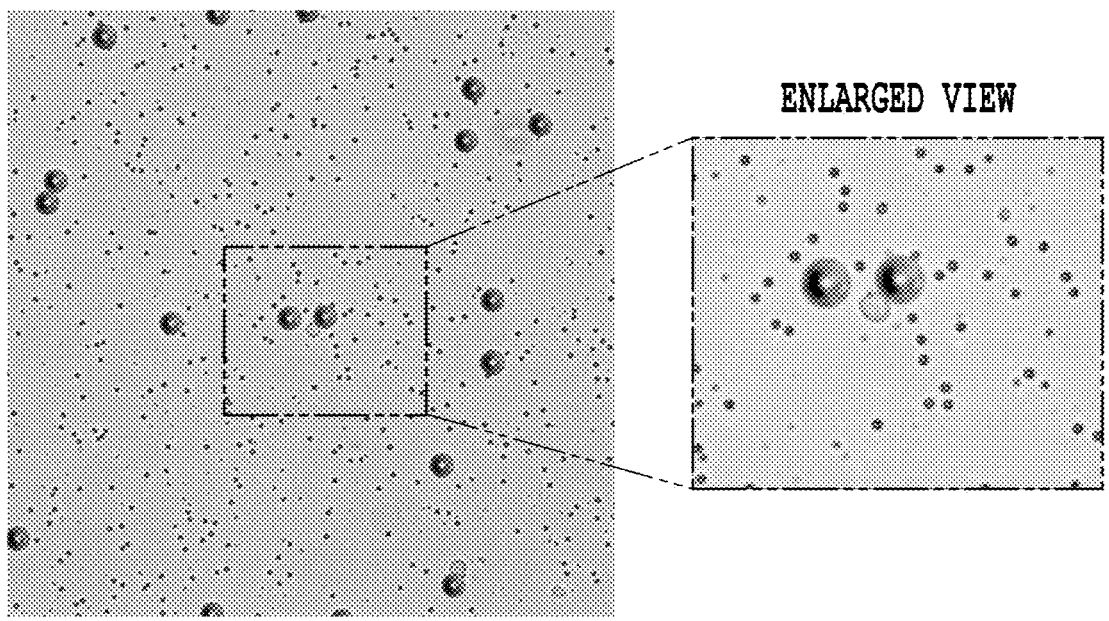
FIG. 22 is a dilute solution of a sample obtained by adding beads made to adhere on a specific antibody to a blood sample, and its enlarged view (before cell separation)
Figure 24:
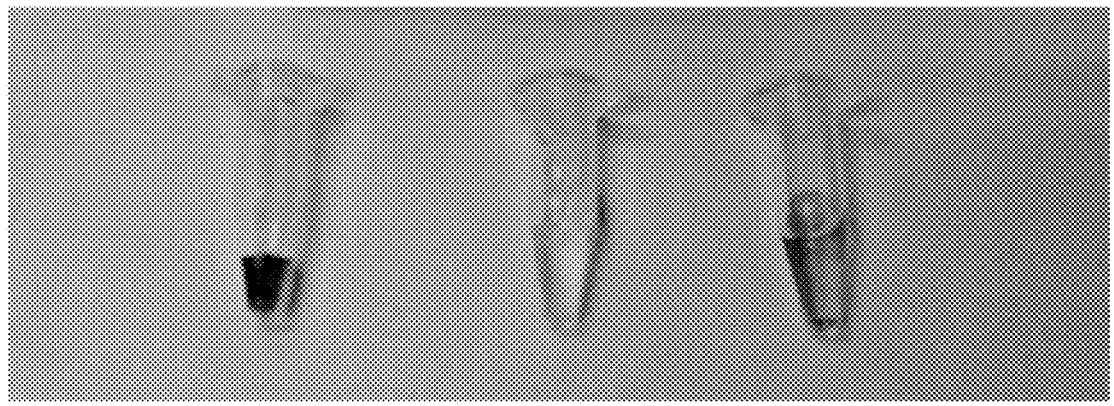
FIG. 24 shows the dilute solution before separation, the targeted cells separated by the cell-separating method of the present invention, and the other blood cells etc.

In the similar way to the aforementioned Example 1, a normal human whole blood (Kohjin Bio Co., Ltd.) was spiked with a human breast cancer-derived cell line (MCF-7) (DS Pharma Biomedical Co., Ltd.) to prepare a mimic cancer patient blood specimen to thereby produce a sample. There was added, to this sample, anti-EpCAM antibody beads (CD326 (EpCAM), Human, pluriBeads, s-beads: pluriSelect Life Science UG & Co.KG) with a particle size of 30 μm carrying a monoclonal antibody against human EpCAM (anti-EpCAM antibody) as a target-capturing molecule, which was incubated while stirring at room temperature to thereby give a sample. The obtained sample was diluted twice with a PBS buffer containing 1% of BSA and 5 mM of EDTA, to which a thrombin inhibitor (PPACK) was added so that its final concentration was 80 μM, and the resulting solution was used as a sample solution (FIG. 22 and FIG. 24 [BEFORE SEPARATION]).

Example 13

The integrated cell-separating device was previously filled with a PBS buffer containing 1% of BSA and 5 mM of EDTA. Then, the sample solution was fed to the sample inlet 31 at a rate of 50 μl/min using a syringe pump. Furthermore, at the same time, the PBS buffer containing 1% of BSA and 5 mM of EDTA was fed to the buffer inlet 32 at a rate of 500 μl/min, and recovered from each recovery port (33, 34).

With respect to the microscopic observation of the recovered sample, the observation of morphology was carried out with a transmission optical microscope. In addition, staining with a nucleated cell staining reagent (Hoechst 33342 solution: Takara Bio Inc.) for staining cancer cells and white blood cells, and staining with an anti-cytokeratin antibody (Anti-pan Cytokeratin antibody [PCK-26] (FITC): Abcam plc.) for staining cancer cells, and staining with an anti-CD45 antibody (Anti-CD45-APC, Mono (ML2): Funakoshi Co., Ltd.) for staining white blood cells were carried out in order to distinguish cells by their properties, and then observation and confirmation under a fluorescence microscope were carried out. An enlarged view of the separation structure portion in the integrated cell-separating device is shown in FIG. 23b.

Figure 23:
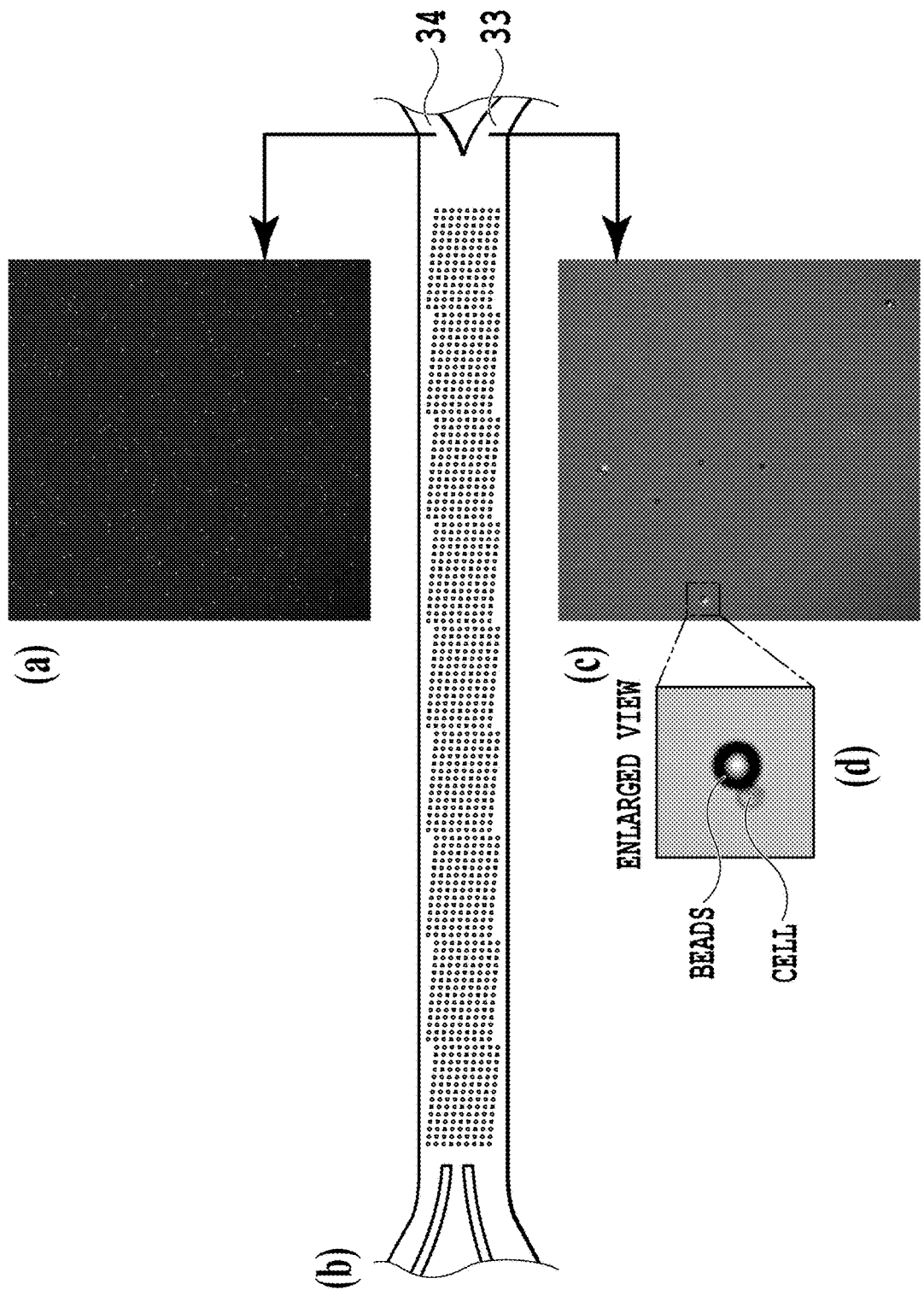
FIG. 23 is a view illustrating that the targeted cell (complex of bead [black] and tumor cell [white]: (c) and enlarged view (d)) is separated from the untargeted cells (red blood cells and the like (a)) by the separation method of the present invention. Note that the photographing conditions between the photographs (c) and (d) are different from each other.

As a result, it was confirmed that, among the components in the whole blood, white blood cells, red blood cells, platelets, and the like were recovered from the second outlet (34) without clogging in the device (FIG. 23a, and FIG. 24 [OTHER BLOOD CELL]). In addition, a human breast cancer-derived cell (MCF-7) having formed a complex together with an anti-EpCAM antibody-labeled beads was selectively discharged from the first outlet (33) (FIG. 23c and FIG. 23d, and FIG. 24 [TARGETED CELL]). In the Example, it was confirmed by microscopy and visual observation that the human breast cancer-derived cell (MCF-7) having formed the complex together with the anti-EpCAM antibody-labeled beads was able to be selectively separated as described above.

Example 14

In the similar way to the aforementioned Example 13, the similar procedure was carried out by the use of a sample obtained by adding a human prostate cancer-derived cell (LNCap) (DS Pharma Biomedical Co., Ltd.) to the normal whole blood instead of the human breast cancer-derived cell (MCF-7), and as a result, it was confirmed that, among the components in the whole blood, white blood cells, red blood cells, platelets, and the like were recovered from the second outlet (34). In addition, the human prostate cancer-derived cell which having formed the complex together with the anti-EpCAM antibody-labeled beads was selectively discharged from the first outlet (33). In the Example, it was confirmed by microscopy that the human prostate cancer-derived cell having formed the complex together with the anti-EpCAM antibody-labeled beads was able to be selectively separated as described above.

Example 15

In the similar way to the aforementioned Example 13, the similar procedure was carried out by the use of a cancer-carrying patient-derived blood instead of the sample in which the human-derived cancer cell was added to the normal whole blood, and as a result, it was confirmed with a microscope that an epithelial tumor cell expressing the EpCAM was able to be accurately separated.

Examples 16 to 18

In the Example 16, the minute aggregate-removing device in which two microchannel structure portions (Structure portion α: pillar intervals are 200 μm, Structure portion β: pillar intervals are 200 μm) were connected in series was connected with the separation structure portion based on the DLD as a separation principle with a separation threshold of 30 μm to thereby fabricate an integrated cell-separating device. Then, as to the samples of the aforementioned Example 13 [human breast cancer-derived cell (MCF-7)], Example 14 [human prostate cancer-derived cell (LNCap)] and Example 15 [cancer-carrying patient-derived blood], the minute aggregates were removed and the cells were separated by the use of this integrated cell-separating device in the similar way (Examples 16 to 18). As a result, it was confirmed that the targeted cell was able to be separated without clogging in all cases.

Examples 19 to 21

In Example 19, alternatively the minute aggregate-removing device in which two microchannel structure portions (Structure portion α: pillar intervals are 300 μm, Structure portion β: pillar intervals are 200 μm) were connected in series was connected with the separation structure portion based on the DLD as a separation principle with a separation threshold of 30 μm to fabricate an integrated cell-separating device. Then, for the samples of the aforementioned Example [human breast cancer-derived cell (MCF-7)], Example 14 [human prostate cancer-derived cell (LNCap)] and Example 15 [cancer-carrying patient-derived blood], the minute aggregates were removed and the cells were separated by the use of this integrated cell-separating device in the similar way (Examples 19 to 21). It was confirmed that the targeted cell was able to be separated without clogging in all cases.

Comparative Examples 5 to 7

As Comparative Examples 5 to 7, a cell-separating device having only a separation structure portion based on the DLD as a separation principle with a separation threshold of 30 μm and having no minute aggregate-removing structure (minute aggregate-removing device) was fabricated, and for the samples used in the aforementioned Examples 13 to 15, the cells were separated in the similar way to Examples 13 to 15. As a result, a small amount of sample could be separated, but in a case where the volume of the solution was increased, clogging was generated in the separation structure portion, and successive separation was not able to be performed.

INDUSTRIAL APPLICABILITY

The cell-separating method, the minute aggregate-removing method, and the device the minute aggregate-removing portion and the cell-separating portion of the present invention can be used for cell separation and purification in a research use, a diagnostic use, pharmaceutical manufacturing, and the like.

REFERENCE SIGNS LIST

1 Cell suspension
2 Targeted cell
3 Untargeted cell
4 Liquid mixture
5 Complex
10 Target-capturing molecule
11 Substance carrying the target-capturing molecule
12 Target-capturing substance
20 Basic structure of DLD microchannel
21 Obstacle structure
22 Particle not smaller than a certain size
23 Particle smaller than a certain size
30 Cell-separating device including the DLD microchannel
31 Sample inlet
32 Buffer inlet
33 First outlet
34 Second outlet
35 Channel space
36 Channel structure portion
37 Flat structure portion
38 Compartment
39 Branch portion
40 Cell-separating device including a fluid feed portion and a recovery portion
41 Sample fluid feed portion
42 Buffer fluid feed portion
43 First recovery portion
44 Second recovery portion
50 Sample
51 Human breast cancer-derived cell
52 White blood cell
53 Red blood cell
54 Platelet
55 Anti-EpCAM antibody-labeled beads
60a Structure portion a
60b Structure portion b
61 Epithelial tumor cell
62 Anti-CD45 antibody-labeled beads
A Outlet A
B Outlet B
C Outlet C
110 Basic structure
111 Structure
112 Minute aggregate
121 Pillar structure portion
130 Minute aggregate-removing device
131 Inlet
132 Outlet
141 Channel structure portion
142 Flat structure portion
143 Channel space
150 Cell-separating device including the minute aggregate-removing structure
151 Minute aggregate-removing structure
152 Cell-separating structure
160 Minute aggregate-removing device used in Examples

The invention claimed is:

1. A method for separating cells depending on sizes from a cell suspension containing two or more kinds of cells, which are targeted cells and untargeted cells, in a continuous fluid flow, the method comprising the steps of:
adding a target-capturing substance that binds a structure on cell surfaces of the targeted cells to the cell suspension to thereby produce complexes of the targeted cells and the target-capturing substance,
introducing the cell suspension containing the complexes into a cell-separating device including a separation area having a deterministic lateral displacement (DLD) microchannel structure, wherein a buffer is added and allowed to flow into a buffer inlet of the cell-separating device, and the cell suspension is added and allowed to flow into a sample inlet and to pass through a plurality of separation areas of the cell-separating device,
separating complexes having sizes not smaller than a determined threshold from the cell suspension, wherein cells having sizes smaller than the threshold move together with the cell suspension flow, and the complexes having the sizes not smaller than the threshold are obliquely displaced to move relative to the flow, thereby being separated, and
recovering the separated complexes from the outlet, wherein the size of the target-capturing substance is 7 to 60 μm, wherein the determined threshold is 20 to 60 μm, wherein the target-capturing substance is composed of a combination body of a target-capturing molecule that binds the structure on the cell surfaces of the targeted cells and a substance carrying the target-capturing molecule.

2. The method for separating cells according to claim 1, wherein the substance carrying the target-capturing molecule is polystyrene or latex.

3. The method for separating cells according to claim 1, wherein the cell suspension is blood.

4. The method for separating cells according to claim 3, wherein the blood is added with 1-(2-Amino-3-phenylpropanoyl)-N-[1-chloro-6-(diaminomethylideneamino)-2-oxohexan-3-yl] pyrrolidine-2-carboxamide (PPACK).

5. The method for separating cells according to claim 1, wherein the targeted cells are tumor cells.

6. The method for separating cells according to claim 1, wherein the cell suspension further contains minute aggregates, the step of removing the minute aggregates from the cell suspension in the continuous fluid flow is further included after the step of producing the complexes and before the step of introducing the cell suspension into the cell-separating device, the removal step is a step in which the cell suspension or a liquid mixture of the cell suspension and the buffer solution is allowed to flow into a minute aggregate-removing device including a removal structure having a second microchannel structure and to pass through the microchannel in the minute aggregate-removing device, thereby capturing the minute aggregates, wherein the second microchannel structure is a plurality of the structures arranged perpendicular to the flow direction of the fluid that is provided at regular intervals parallel to the flow direction.

7. The method for separating cells according to claim 1, wherein the second microchannel structure is composed of pillars arranged at intervals wider than 30 μm.

\* \* \* \* \*